(12) United States Patent
Sebastian et al.

(10) Patent No.: US 9,315,851 B2
(45) Date of Patent: *Apr. 19, 2016

(54) METHODS, PEPTIDES, AND BIOSENSORS USEFUL FOR DETECTING A BROAD SPECTRUM OF BACTERIA

(71) Applicant: Woundchek Laboratories (US), Inc., Fall River, MA (US)

(72) Inventors: Shite Sebastian, Somerville, MA (US); Gerard J. Colpas, Holden, MA (US); Diane L. Ellis-Busby, Lancaster, MA (US); Jennifer M. Harvard, Framingham, MA (US); Mitchell C. Sanders, West Boylston, MA (US)

(73) Assignee: Woundchek Laboratories (US), Inc., Fall River, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/575,898

(22) Filed: Dec. 18, 2014

(65) Prior Publication Data

US 2015/0184220 A1    Jul. 2, 2015

Related U.S. Application Data

(60) Continuation of application No. 14/106,149, filed on Dec. 13, 2013, now abandoned, which is a division of application No. 10/576,633, filed as application No. PCT/US2004/036600 on Nov. 3, 2004, now Pat. No. 8,609,358.

(60) Provisional application No. 60/578,811, filed on Jun. 9, 2004, provisional application No. 60/516,692, filed on Nov. 3, 2003.

(51) Int. Cl.
| C12Q 1/37 | (2006.01) |
| C12Q 1/04 | (2006.01) |
| G01N 33/543 | (2006.01) |
| G01N 33/569 | (2006.01) |
| C07K 7/08 | (2006.01) |
| C07K 14/00 | (2006.01) |

(52) U.S. Cl.
CPC ... *C12Q 1/37* (2013.01); *C07K 7/08* (2013.01); *C07K 14/001* (2013.01); *C12Q 1/04* (2013.01); *G01N 33/543* (2013.01); *G01N 33/56911* (2013.01); *G01N 2333/8121* (2013.01)

(58) Field of Classification Search
None
See application file for complete search history.

(56) References Cited

U.S. PATENT DOCUMENTS

| 4,242,447 | A | 12/1980 | Findl et al. |
| 4,259,442 | A | 3/1981 | Gayral |
| 4,897,444 | A | 1/1990 | Brynes et al. |
| 5,210,022 | A | 5/1993 | Roth et al. |
| 5,236,827 | A | 8/1993 | Sussman et al. |
| 5,330,889 | A | 7/1994 | Monget |
| 5,512,445 | A | 4/1996 | Yang et al. |
| 5,518,894 | A | 5/1996 | Berg |
| 5,523,205 | A | 6/1996 | Cossart et al. |
| 5,662,905 | A | 9/1997 | Siadak et al. |
| 5,716,799 | A | 2/1998 | Rambach |
| 5,719,031 | A | 2/1998 | Haugland et al. |
| 5,783,410 | A | 7/1998 | He et al. |
| 5,804,395 | A | 9/1998 | Schade et al. |
| 5,824,468 | A | 10/1998 | Scherer et al. |
| 5,932,415 | A | 8/1999 | Schubert et al. |
| 5,976,827 | A | 11/1999 | Jeffrey et al. |
| 5,994,059 | A | 11/1999 | Hogan et al. |
| 6,048,688 | A | 4/2000 | Korth et al. |
| 6,051,391 | A | 4/2000 | Schabert et al. |
| 6,207,430 | B1 | 3/2001 | Yaver et al. |
| 6,235,285 | B1 | 5/2001 | Burnham |
| 6,284,517 | B1 | 9/2001 | Restaino |
| 6,342,581 | B1 | 1/2002 | Rosen et al. |
| 6,380,370 | B1 | 4/2002 | Doucette-Stamm et al. |
| 6,387,650 | B1 | 5/2002 | Townsend et al. |
| 7,566,564 | B2 * | 7/2009 | Colpas et al. ............. 435/287.1 |
| 2003/0096315 | A1 | 5/2003 | Sanders |

(Continued)

FOREIGN PATENT DOCUMENTS

| EP | 0122028 | 10/1984 |
| EP | 0428000 | 5/1991 |

(Continued)

OTHER PUBLICATIONS

Altekruse et al., "Cheese-Associated Outbreaks of Human illness in the United States, 1973 to 1992: Sanitary Manufacturing Practices Protect Consumers", J. Food Prot., 61(10):1405-1407 (1998).
BBC News, Health, "Smart bandage 'spots infection'", [online] Nov. 5, 2001 [retrieved on Jan. 23, 2002] Retrieved from the Internet URL: http://news.bbc.co.uk/hi/english/health/newsid_1634000/1634639.stm.
Braun et al., "Excretion of a Protease by Serratia Marcescens", Arch. Microbiol., 124:55-61 (1980).
Cormican et al., "Detection of Extended-Spectrum β-Lactamase (ESBL)-Producing Strains by the Etest ESBL Screen", J. Clinical Microbiology 34(8):1880-1884 (1996).
Dalton et al., "An Outbreak of Gastroenteritis and Fever Due to Listeria Monocytogenes in Milk", N. Engl. J. Med., 336 (2):100-105 (1997).

(Continued)

*Primary Examiner* — Oluwatosin Ogunbiyi
(74) *Attorney, Agent, or Firm* — McDonnell Boehnen Hulbert & Berghoff LLP

(57) ABSTRACT

Described herein are methods of detecting a wound infection and for detecting the presence or absence of bacteria, for example, wound bacteria in a sample, by contacting a sample with a peptide substrate derived from the modification of the reactive site loop (RSL) domain of the α1-proteinase inhibitor. In the current invention, we have demonstrated that these peptide substrates without the alpha 1 protein can be efficiently used as peptide substrates. The modification or the absence of modification of this peptide substrate by the enzyme produced and/or secreted by the bacteria, can serve as an indicator for the presence or absence of the bacteria in the sample. The present invention also features a biosensor for detecting the presence or absence of bacteria in a sample.

15 Claims, 29 Drawing Sheets

(56) References Cited

U.S. PATENT DOCUMENTS

| | | |
|---|---|---|
| 2005/0142622 A1 | 6/2005 | Sanders et al. |
| 2005/0181465 A1 | 8/2005 | Sanders |

FOREIGN PATENT DOCUMENTS

| | | |
|---|---|---|
| EP | 0430608 | 6/1991 |
| EP | 0864864 | 9/1998 |
| JP | 11178567 | 7/1999 |
| JP | 2000093195 | 4/2000 |
| JP | 2001169799 | 6/2001 |
| JP | 2001299381 | 10/2001 |
| WO | 91/16336 | 10/1991 |
| WO | 97/28261 | 8/1997 |
| WO | 00/50872 | 8/2000 |
| WO | 00/63394 | 10/2000 |
| WO | 01/59149 | 8/2001 |
| WO | 02/10433 | 2/2002 |
| WO | 03/063693 | 8/2003 |
| WO | WO 03/063693 * | 8/2003 |
| WO | 2004/080148 | 9/2004 |
| WO | 2004/087942 | 10/2004 |
| WO | 2005/012556 | 2/2005 |
| WO | 2005/021780 | 3/2005 |
| WO | 2005/042770 | 5/2005 |
| WO | 2005/042771 | 5/2005 |

OTHER PUBLICATIONS

Decedue et al., "Purification and Characterization of the Extracellular Proteinase of Serratia Marcescens", Biochem. et Biophysica Acta/. 569:293-301 (1979).

Domann et al., "Molecular Cloning, Sequencing, and Identification of a Metalloprotease Gene from Listeria monocytogens That is Species Specific and Physically Linked to Listeriolysin Gene", Infection and Immunity, 59(1):65-72 (1991).

Engel et al., "Pseudomonas aeruginosa Protease IV Produces Corneal Damage and Contributes to Bacterial Virulence", Invest. Opthalmol. Vis. Sci., 39(3):662-665 (1998).

Engels et al., "Secretion of staphylocoagulase by *Staphylococcus aureus*: the role of a cell-bound intermediate," Antonie Van Leeuwenhoek, 47(6):509-527 (1981).

Ericsson et al., "An Outbreak of Listeriosis Suspected to Have Been Caused by Rainbow Trout", J. Clin. Microbiol., 35(11):2904-2907 (1997).

From the Centers for Disease Control and Prevention, "Update: Multistate Outbreak of Listeriosis-United States, 1998-1999", JAMA, 281(4):317-318 (1999).

Glaser et al., "Comparative Genomics of Listeria Species", Science, 294:849-852 (2001).

Gottesman, "Proteases and Their Targets in *Escherichia coli*", Annu. Rev. Genet., 30:465-506 (1996).

Hadiziyannis et al., "Screening and confirmatory testing for extended spectrum β-lactamases (ESBL) in *Escherichia coli*, Klebsiella pneumoniae and Klebsiella oxytoca clinical isolates", Diagnostic Microbiology and Infectious Disease, 36:113-117 (2000).

Häse et al., "Bacterial Extracellular Zinc-Containing Metalloproteases", Microbiological Reviews, 57(4):823-837 (1993).

Keelan et al., "Multitest System for Biochemical Identification of Salmonella, *Escherichia coli*, and Ogther Enterobacteriaceae Isolated from Foods: Collaborative Study", J. Assoc. Off. Anal. Chem., 71(5):968-972 (1988).

Kennedy et al., "Mechanism of Hydrolysis of O-Nitrophenyl-β-Galactoside in *Staphylococcus aureus* and Its Significance for Theories of Sugar Transport", Proc. Natl. Acad. Sci. USA, 58:225-228 (1967).

Liu et al., "Use of a Fluorescence Plate Reader for Measuring Kinetic Parameters with Inner Filter Effect Correction", Anal. Biochem., 267:331-335 (1999).

Maeda, "Role of Microbial Proteases in Pathogenesis", Microbiol. Immunol., 40(10): 685-699 (1996).

Marquis et al., "Proteolyitc Pathways of Activation and Degradation of a Bacterial Phospholipase C during Intracellular Infection by Listeria monocytogenes", J. Cell Biol. 137(6):1381-1392 (1997).

McAleese et al., "Loss of Clumping Factor B Fibrinogen Binding Activity by *Staphylococcus aureus* Involves Cessation of Transcription, Shedding and Cleavage by Metallaprotease", J. Biol. Chem., 276(32):29969-29978 (2001).

Molla et al., "Characterization of 73 kDa Thiol Protease from Serratia Marcescens and Its Effect on Plasma Proteins", J. Biochem., 104:616-621 (1988).

Molla et al., "Degradation of Protease Inhibitors, Immunoglobulins, and other Serum Proteins by Serratia Protease and Its Toxicity to Fibroblasts in Culture", Infection and Immunity, 53(3):522-529 (1986).

Nelson et al., "Inactivation of β1-Proteinase Inhibitor As a Broad Screen for Detecting Proteolytic Activities in Unknown Samples", Analytical Biochemistyry, 260(2):230-236 (1998).

O'Riordan et al., "Listeria Intracellular Growth and Virulence Require Host-Derived Lipoic Acid", Science, 302:462-464 (2003).

Okuno et al., "An analysis of target preferences of *Escherichia coli* outer-membrane endoprotease OmpT for use in therapeutic peptide production: efficient cleavage of substrates with basic amino acids at the P4 and P6 positions", Biotechnology and Applied Biochemistry, 36:77-84 (2002).

Oshida et al., "A *Staphylococcus aureus* autolysin that has an N-acetylmuramoyl-L-alaine amidase domain and an endo-β-N-acetylglucosaminidase domain: Cloning, sequence analysis, and characterization", Proc. Natl. Acad. Sci. USA, 92:285-289 (1995).

Pallen et al., "The HtrA family of serine proteases", Mol. Microbiol., 26(2):209-221 (1997).

Peterson et al., "Insight into the Mechanism of Serpin-Proteinase Inhibition from 2D [1H-15N] NMR Studies of the 69 kDa α1-Proteinase Inhibitor Pittsburgh-Trypsin Covalent Complex", Biochemistry, 40(21):6284-6292 (2001).

Piorunska-Stolzmann et al., "Serum Glycerol Ester Hydrolase Activity is Related to Zinc and Copper Concetrations in Atherosclerosis Obliterans and Aneurysm", J. Trace Elem. Med. Biol. 12:39-43 (1998).

Poyart et al., "The Zinc Metalloprotease of Listeria monocytogenes in Required for Maturation of Phosphatidylcholine Phospholipase C: Direct Evidence Obtained by Gene Complementation", Infect. and Immun. 61(4):1576-1580 (1993).

Putsep et al., "Germ-free and Colonized Mice Generate the Same Products from Enteric Prodefensins", J. Biol. Chem., 275(51):40478-40482 (2000).

Rice et al., "Description of *Staphylococcus* Serine Protease (ssp) Operon in *Staphylococcus aureus* and Nonpolar Inactivation of sspA-Encoded Serine Protease", Infection and Immunity, 69(1):159-169 (2001).

Rodriguez et al., "Evaluation of proteolytic activity of micro-organisms isolated from dry cured ham", J. Appl. Mcirobiol., 85:905-912 (1998).

Rosenstein et al., "Staphylococcal lipases: Biochemical and molecular characterization", Biochimie, 82:1005-1014 (2000).

Salamone et al., "Production purification and characterization of a 50-kDa extracellular metalloprotease from Serratia marcescens", Appl. Microbiol. Biotechnol., 48:317-324 (1997).

Schwartz et al., "Bidning and Assembly of Actin Filaments by Plasma Memebranes from Dictyostelium discoideum", J. Cell Biol., 102:2067-2075 (1986).

Shikata et al., "Detection of Large COOH-Terminal Domains Processed fromt he Precursor of Serratia marcescens Serine Protease in the Outer Membrane of *Escherichia coli*", J. Biochem., 111:627-632 (1992).

Smith et al., "The Tandem Repeat Domian in the Listeria monocytogenes ActA Protein Controls the Rate of Actin-based Motility, the Percentage of Moving Bacteria, and the Localization of Vasodilator-stimulated Phosphoprotein and Profilin", J. Cell Biol., 135(3):647-660 (1996).

Sugai et al., "Identification of Endo-β-N-Acetylglucosaminidase and N-Acetylumuramyl-L-Alanine Amidase as Cluster-Dispersing Enzymes in *Staphylococcus aureus*", J. Bacteriol., 177(6):1491-1496 (1995).

(56) References Cited

OTHER PUBLICATIONS

Suter et al., "Proteolytic Inactivation of al Proteinase Inhibitor in Infected Bronchial Secretions from Patients with Cystic Fibrosis", European Respiratory Journal, 4(1):40-49 (1991).
Thomspon et al., "Rapid Biochemical Test to Identify Verocytotoxin-Positive Strains of *Escherichia coli* Serotype O157", J. Clin. Microbiol. 28(10):2165-2168 (1990).
Ton-That et al., "Anchor Structure of Staphylococcal Surface Proteins", J. Biol. Chem., 273(44):29143-29149 (1998).
Trivet et al., "Citrate Cycle and Related Metabolism of Listeria monocytogenes", J. Bacteriol., 107(3):770-779 (1971).
van Kampen et al., "Modifying the Substrate Specificity of Staphylococcal Lipases", Biochem., 38:9524-9532 (1999).
Vollmer et al., "Novel Pathogenic Mechanism of Microbial Metalloproteinases: Liberation of Membrane-Anchored Molecules in Biologically Active Form Exemplified by Studies with the Human Interleukin-Receptor", Infection and Immunity, 64(9):3646-3651 (1996).
Wang et al., "Analysis of Cytoskeletal Structures by the Microinjection of Fluorescent Probes", Noninvasive Techniques in Cell Biology, pp. 177-212 (1990).
Yolken, "Enzymic Analysis for Rapid Detection of Microbial Infection in Human Body Fluids: An Overview", Clin. Chem. 27(9):1490-1498 (1981).
Zahner et al., "The *Streptococcus pneumoniae* Beta-Galctosidase is a Surface Protein", J. Bacteriol., 182 (20):5919-5921 (2000).
Zhong et al., "Development of an Internally Quenched Fluorescent Substrate for *Escherichia coli* Leader Peptidase", Analytical Biochemistry, 255:66-73 (1998).
Xue et al., "Pro-inflammatory cytokinelchemokine gene expression in human comeal epithelial cells colonized by Pseudomonas aerguinosa", Clinical and Experimental Opthalmology, 28(3):197-200 (2001).
Bowie et al., "Deciphering the Message in Protein Sequences: Tolerance to Amino Acid Substitutions", Science, 247 (4948):1306-1310 (1990).
Lazar et al., "Transforming Growth Factor α: Mutation of Aspartic Acid 47 and Leucine 48 Results in Different Biological Activities", Molecular and Cellular Biology, 8(3):1247-1252 (1988).
Burgess et al., "Possible Dissociation of the Heparin-binding and Mitogenic Activities of Heparin-binding (Acidic Fibroblast) Growth Factor-1 from its Receptor-binding Activities by Site-directed Mutagenesis of a Single Lysine Residue", the Journal of Cell Biology, 111:2129-2138 (1990).
Jarvik et al., "Epitope Tagging", Annu. Rev Genet., 32:601-618 (1998).
Ngamkitidechakul et al., "Sufficiency of the Reactive Site Loop of Maspin for Induction of Cell-Matrix Adhesion and Inhibition of Cell Invasion", JBC, 278(34):31796-31806 (2003).
Schick et al., "The reactive site loop of the serpin SCCA1 is essential for cysteine proteinase inhibition", Proc. Natl. Acad. Sci., 95:13465-13470 (1998).
Steffensen, "Proteolytic Events of Wound-Healing—Coordinated Interactions among Matrix Metalloproteinases (MMPs), Integrins, and Extracellular Matrix Molecules", Crit. Rev. Oral. Biol. Med, 12(5):373-398 (2001).
Armstrong et al., "The Role of Matrix Metalloproteinases in Wound Healing", J. Am. Podiatr. Med. Assoc., 92(1):12-18 (1998).
Ungar et al., "Further Studies on the Role of Proteases in the Allergic Reaction", J. Exp Med., 113(2):359-380 (1961).
Desrochers et al., "Interstitial Collagenase (Matrix Metallopreteinase-1) Expresses Serpinase Activity", J Clin. Invest., 88:2258-2265 (1991).
Kamalakkannan eta L, "Bacterial lipid modification of proteins of novel protein engineering applications", Protein Engineering, Design and Selection, 17(10):721-729 (2004).
Fontana et al., "Twelve Aberrant Strains of *Staphylococcus aureus* subsp. aureus from Clinical Specimens", J. Clin. Micrbiol., 31(8):2105-2109 (1993).
Gaillot et al., "Evaluation of CHROMagar *Staph. aueus*, a New Chromogenic Medium, for Isolation and Presumptive Identification of *Staphylococcus* from Human Clinical Specimens", J. Clin. Microbiol., 38(4):1587-1591 (2000).
Perry et al., "ABC Medium, a New Chromogenic Agar for Selective Isolation of *Salmonella* spp.", J. Clin. Microbiol., 37 (3):766-768 (1999).
http://en.wikipedia.org/wiki/Oxidase_test, Jul. 20, 2007.
http://en.wikipedia.org/wiki/Nitrate)reductase_test, Jul. 20, 2007.
http://en.wikipedia.org/wiki/Indole_test, Jul. 20, 2007.
http://en.wikipedia.org/wiki/GUS_reporter_system, Jul. 20, 2007.
http://www.bact.wisc.edu/microtextbook/index.php?module+Book&func=displayarticle&art_id=119, Jul. 20, 2007.
Nair, et al., "ClpE, a Novel Member of the HSP100 Family, is Involved in Cell Division and Virulence of Listeria monocytogenes", Mol. Microbiol., 31(1):185-196 (1999).

\* cited by examiner

Edans—E A A G A M F L E A I P K—Dabcyl

CPI1

K G T E A A G A M F L E A I P M S I P P E V K

Alpha-1 proteinase inhibitor (human)

Edans—E G A M F L E A I P M S I P K—Dabcyl

CPI2

Figure 1B

METHODS, PEPTIDES, AND BIOSENSORS USEFUL FOR DETECTING A BROAD SPECTRUM OF BACTERIA

BACKGROUND OF THE INVENTION

Infection of wounds is a major source of healthcare expenditure in the United States. Approximately 5% of all surgical wounds become infected with microorganisms, and that figure is considerably higher (10-20%) for patients undergoing abdominal surgery. Bacterial species, such as Staphylococci are the most frequently isolated organisms from infected wounds. This is probably because humans are the natural reservoir for staphylococci in the environment, with up to 50% of the population colonized at any given time. Colonization rates are significantly higher in the hospital setting, both among healthcare workers, and among patients. Moreover, the colonizing organisms in the hospital environment are likely to be resistant to many forms of antimicrobial therapy, due to the strong selective pressure that exists in the nosocomial environment, where antibiotics are frequently used. Staphylococci are usually carried as harmless commensals, however given a breach in the epidermis, they can cause severe, even life threatening infection.

Staphylococci are the most common etiologic agents in surgical wound infections; others include, but are not limited to *Streptococcus pyogenes*. *Pseudomonas aeruginosa, Enterococcus faecalis, Serratia marcescens, Proteus mirabilis, Enterobacter clocae, Acetinobacter anitratus, Klebsiella pneumoniae*, and *Escherichia coli*. Post-surgical infection due to any of the above organisms is a significant concern of hospitals. The most common way of preventing such infection is to administer prophylactic antibiotic drugs. While generally effective, this strategy has the unintended effect of breeding resistant strains of bacteria. The routine use of prophylactic antibiotics should be discouraged for the very reason that is encouraging the growth of resistant strains.

Rather than using routine prophylaxis, a better approach is to practice good wound management, i.e., keep the area free from bacteria before, during, and after surgery, and carefully monitor the site for infection during healing. Normal monitoring methods include close observation of the wound site for slow healing, signs of inflammation and pus, as well as measuring the patient's temperature for signs of fever. Unfortunately, many symptoms are only evident after the infection is already established. Furthermore, after a patient is discharged from the hospital they become responsible for monitoring their own healthcare, and the symptoms of infection may not be evident to the unskilled patient.

A system or biosensor that can detect a broad spectrum of bacteria, especially during the early stages of infection before symptoms develop, would be advantageous to both patients and healthcare workers. If a patient can accurately monitor the condition of a wound after hospital/clinic discharge, then appropriate antimicrobial therapy can be initiated early enough to prevent a more serious infection.

SUMMARY OF THE INVENTION

It has been found that a synthetic enzyme substrate, human alpha-1 protease inhibitor, can be used in a test system to identify multiple microorganism species, such as bacteria, that commonly infect wounds.

Human alpha-1 proteinase inhibitor ($\alpha$1-PI) is a member of the serpin family. Serpins are a family of serine proteinase inhibitors that function as irreversible suicide substrates resulting in the inhibition of proteinases. Proteases are a common virulence factor in pathogenic bacteria, and are sometimes used to disable the host defenses. Of the serpin family (inhibitors is already inherent in the name serpin), alpha-1-proteinase inhibitor ($\alpha$1-PI) is one of the major and most well-studied members. $\alpha$1-PI is involved in the regulation of elastases secreted from activated neutrophils, which in turn control the degradation of the host connective tissue (Salvesen, G S et al., "Human plasma proteinase inhibitors", *Ann. Rev. Biochem.*, 52: 655-709 (1983), incorporated herein by reference). This unique category of serine proteinase inhibitors possesses a characteristic exposed reactive site loop (RSL) domain. Importantly, the RSL of $\alpha$1-PI has been demonstrated to be susceptible to cleavage by a number of proteinases of both host and bacterial origin, resulting in the inactivation of $\alpha$1-PI.

The test system can be designed to simultaneously identify multiple (for example, at least 2, at least 5, or at least 10) different microorganism species, such as those that commonly infect wounds. For example, it can identify those enzymes that are common to certain classes of pathogenic bacteria, but which are not present in non-pathogenic bacteria. Such enzymes can be identified, for example, with a computer based bioinformatics screen of the bacterial genomic databases. By using enzymes as the basis for detection systems, very sensitive tests can be designed, since even a very small amount of enzyme can catalyze the turnover of a substantial amount of substrate.

Accordingly, the present invention features a method of detecting the presence or absence of one or more microorganisms, for example, a bacterium, in a sample by detecting the presence or absence of a molecular marker for the bacterium in the sample.

A "molecule marker" is any molecule which can be used for the detection of the presence or absence of a microorganism (e.g., a bacterium, fungus or virus) in a sample, such as a wound or body fluid. In particular, the molecular markers to be detected include proteins, such as proteins secreted by microorganisms, expressed on the cell surface of microorganisms, or expressed on the surface of a cell infected with a virus or prion. In one embodiment, the enzyme is a bacterial protease.

In one aspect, the invention features a method for detecting the presence or absence of one or more bacteria in a sample, comprising the steps of contacting the sample with a detectably labeled synthetic serpin reactive site loop (RSL) domain peptide substrate, under conditions that result in modification of the substrate by an enzyme produced and/or secreted by the bacterium; and detecting the modification or the absence of the modification of the substrate. Modification of the substrate indicates the presence of the bacterium in the sample, and the absence of modification of the substrate indicates the absence of the bacterium in the sample.

The substrate can be synthetic. For example, it can be derived from a native or non-naturally occurring RSL domain and can have the same or equivalent activity as the RSL of a wild type serpin. It can also comprise or consist of a variant, analog or fragment of a serpin RSL domain. In one embodiment, the substrate comprises SEQ ID NO: 1, 2 or 3. In one embodiment, the substrate is CPI1, CPI2 or CPI3, as described below.

The bacterium can be, for example, a wound specific bacterium, such as *Staphylococcus aureus, Staphylococcus epidermidis, Streptococcus pyogenes, Pseudomonas aeruginosa, Enterococcus faccalis, Serratia marcescens, Proteus mirabilis, Enterobacter clocae, Acetinobacter anitratus, Klebsiella pneumonia*, and *Escherichia coli*.

In another aspect, the present invention features a method for detecting the presence or absence of a wound infection in a subject, comprising the steps of a) contacting a sample obtained from a wound in a subject with a detectably labeled synthetic serpin RSL domain peptide substrate under conditions that result in modification of the substrate by an enzyme produced and/or secreted by a bacterium; and b) detecting a modification or the absence of a modification of the substrate. Modification of the substrate indicates the presence of a wound infection in the subject, and the absence of modification of the substrate indicates the absence of an infection in the subject.

In yet another aspect, the present invention features a method for detecting the presence or absence of a wound infection in a subject, comprising the steps of a) contacting a wound in a subject with a detectably labeled synthetic serpin RSL domain peptide substrate, for an enzyme produced and/or secreted by a bacterium, under conditions that result in modification of the substrate by an enzyme produced and/or secreted by the bacterium; and b) detecting a modification or the absence of a modification of the substrate. Modification of the substrate indicates the presence of a wound infection in the subject, and the absence of modification of the substrate indicates the absence of an infection in the subject.

In another aspect, the invention features a biosensor for detecting the presence or absence of a bacterium, for example, a wound-specific bacteria in a sample, comprising a solid support and a detectably labeled synthetic serpin RSL domain peptide substrate, wherein the substrate is attached to the solid support. The peptide may be labeled with fluorescent or colorimetric dyes for detection of peptide cleavage by a bacterial protease.

In still another aspect, the present invention features a kit for detecting a wound infection, comprising a biosensor for detecting the presence or absence of a bacterium in a sample, and one or more reagents for detecting the presence of the bacterium that is the causative agent of the wound infection. For example, the reagent can be used to detect an enzyme secreted by a bacterium. In particular, the reagent can be used to detect the modification of the substrate of the biosensor.

BRIEF DESCRIPTION OF THE DRAWINGS

FIGS. 1A and 1B. FIG. 1A depicts the relative position of the cleavage sites on the alpha-1-proteinase inhibitor (α1-PI) RSL sequence (SEQ ID NO:4). FIG. 1B depicts the sequences of the CPI1 peptide (SEQ ID NO:1), the CPI2 peptide (SEQ ID NO:2) and the alpha-1 proteinase inhibitor (human) (SEQ ID NO:3).

FIGS. 2A and 2B are graphs of the relative fluorescence of samples containing overnight bacterial culture, assay substrate (FIG. 2A, CPI1 Peptide; FIG. 21, CPI2 Peptide), and reaction buffer (pH 7.2) with 150 mM NaCl over time (in seconds). FIGS. 2C and 2D are graphs of the relative fluorescence of samples containing overnight bacterial supernatant, assay substrate (FIG. 2C, CPI1 Peptide; FIG. 2D, CPI2 Peptide), and reaction buffer (pH 7.2) with 150 mM NaCl over time (in seconds).

FIGS. 3A and 3B are graphs of the relative fluorescence of samples containing 48 hour bacterial culture, assay substrate (FIG. 3A, CPI1; FIG. 3B, CPI2), and reaction buffer over time (in seconds). FIGS. 3C and 3D are graphs of 2745363 t the relative fluorescence of samples containing 48 hour bacterial supernatant, assay substrate (FIG. 3C, CPI1; FIG. 3D, CPI2), and reaction buffer over time (in seconds).

FIG. 4A shows images of sensors incubated with bacteria under 365 nm UV light source. FIG. 4B shows intensity data from each concentration obtained from digitized photo.

FIG. 5B shows intensity data from each concentration obtained from digitized photo.

FIG. 6A shows images of sensors incubated with bacteria under 365 nm UV light source. FIG. 6B shows intensity data from each concentration obtained from digitized photo.

FIG. 7A shows images of sensors incubated with bacteria under 365 nm UV light source. FIG. 7B shows intensity data from each concentration obtained from digitized photo.

FIG. 8A shows images of sensors incubated with bacteria under 365 nm UV light source. FIG. 8B shows intensity data from each concentration obtained from digitized photo.

DETAILED DESCRIPTION OF THE INVENTION

As part of their normal growth processes, many microorganisms secrete a number of enzymes into their growth environment. These enzymes have numerous functions including, but not limited to, the release of nutrients, protection against host defenses, cell envelope synthesis (in bacteria) and/or maintenance, and others as yet undetermined. Many microorganisms, such as bacteria, also produce enzymes on the cell surface that are exposed to (and interact with) the extracellular environment.

A system that can detect the presence of these enzymes that are produced and/or secreted can equally serve to indicate the presence of the producing/secreting bacteria. Alternatively, a system that can detect the absence of these enzymes that are produced and/or secreted can equally serve to indicate the absence of the producing/secreting bacteria. Such a detection system is useful for detecting or diagnosing an infection, for example, a wound infection.

Figure 1A:
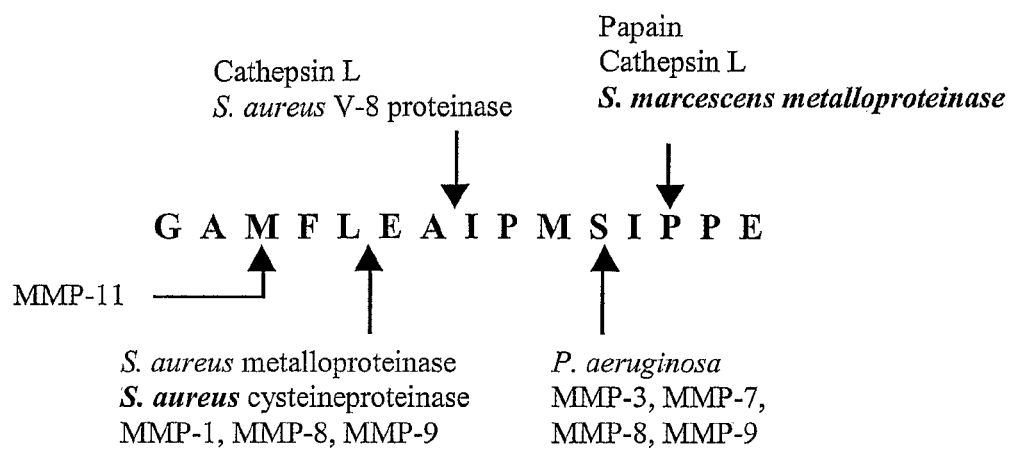

The present invention pertains to the use of substrates, such as synthetic serpin RSL domain peptide substrates, to detect the presence or absence of enzymes produced or secreted by a broad spectrum of bacteria. As used herein, "synthetic" refers to a non-naturally occurring peptide. The synthetic peptides can be derived from (e.g., a variant, analog or fragment of) a full-length or wild-type reactive site loop (RSL) of a member of the serpin family (e.g., α1-PI). In one embodiment, the synthetic peptide substrate is prepared according to the methods exemplified herein. These synthetic substrates can be then labeled with a detectable label such that under conditions wherein their respective enzymes specifically react with them, they undergo a modification, for example, a visible color change that is observed. Substrates for use in the present invention include any molecule, either synthetic or naturally-occurring, such as a molecule comprising a cleavage site of the RSL sequence, that can interact with an enzyme of the present invention. The relative position of the cleavage sites on the RSL sequence of the alpha-1-proteinase inhibitor (α1-P1) has been previously reported (Nelson, D. et al., "Inactivation of alpha1-proteinase inhibitor as a broad screen for detecting proteolytic activities in unknown samples," *Anal. Biochem*, 260(2):230-36 (1998)) and is represented in FIG. 1A, Examples of substrates include those substrates described herein, as well as substrates for these enzymes that are known in the art. In one embodiment, the substrate comprises the sequence EAAGAMFLEAIPK (SEQ ID NO:1). In another embodiment, the substrate comprises EGAMFLEA-IPMSIPIK (SEQ ID NO:2), Other examples include α1-PI derived fluorescent peptides, for example, Edans-EAAGAM-FLEAIPK-Dabcyl (CPI1) (SEQ ID NO:1) and Edans-EGAMFLEAIPMSIPK-Dabcyl (SEQ ID NO:2) (FIG. 1B).

Substrates for use in the present invention also include colorimetric and or fluorometric components and a peptide, and interact with at least one protein produced by and/or secreted by a microorganism. In some embodiments, the peptide portion of the substrate interacts with the protein of the microorganism. In other embodiments, at least one colorimetric component portion of the substrate interacts with the protein of the microorganism.

Examples of substrates are described in PCT application PCT/US03/03172 entitled "Method For Detecting Microorganisms" by Mitchell C. Sanders, et al. filed on Jan. 31, 2003, and published as WO 03/063693 on Aug. 7, 2003; and U.S. Application No. 60/578,502 entitled "Colorimetric Substrates, Colorimetric Sensors, and Methods of Use," by Mitchell C. Sanders. et al. filed on Jun. 9, 2004. The entire teachings of these applications are incorporated herein by reference.

The synthetic serpin RSL domain peptide substrate can be used to detect multiple (i.e., more than one, e.g., at least 2, 3, 4, 5, 10, 15, 20, 25 or more) wound pathogens, such as bacteria. The enzymes that are used in the bacteria detection method of the present invention are preferably wound-specific enzymes. As used herein, a wound-specific enzyme is an enzyme produced and/or secreted by pathogenic bacteria, but is not produced and/or secreted by non-pathogenic bacteria. Examples of pathogenic bacteria include, but are not limited to, *staphylococcus* (for example, *Staphylococcus aureus, Staphylococcus epidermidis*, or *Staphylococcus saprophyticus*), *streptococcus* (for example, *Streptococcus pyogenes, Streptococcus pneumoniae*, or *Streptococcus agalactiae*). *enterococcus* (for example, *Enterococcus faecalis*, or *Enterococcus faecium*), corynebacteria species (for example, *Corynebacterium diptheriae*), bacillus (for example, *Bacillus anthracis*), listeria (for example, *Listeria monocytogenes*), *Clostridium* species (for example, *Clostridium perfringens*, *Clostridium tetanus, Clostridium botulinum, Clostridium difficile*), *Neisseria* species (for example, *Neisseria meningitidis*, or *Neisseria gonorrhoeae*), *E. coli, Shigella* species, *Salmonella* species, *Yersinia* species (for example, *Yersinia pestis, Yersinia pseudoruberculosis*, or *Yersinia enterocolitica*), *Vibrio cholerae, Campylobacter* species (for example, *Campylobacterjejuni* or *Cainpylobacter fetus*), *Helicobacter pylori*, pseudomonas (for example, *Pseudomona aeruginosa* or *Pseudomonas mallei*), *Haemophilus influenzae, Borderella perrussis, Mycoplasma pneumoniae, Ureaplasma urealyticum, Legionella pneumophila, Treponema pallidum, Leptospira interrogans, Borrelia burgdorferi*, mycobacteria (for example, *Mycobacterium tuberculosis*), *Microbacterium leprae, Actinoinyces* species, *Nocardia* species, chlamydia (for example, *Chlamydia psittaci, Chlamydia trachomatis*, or *Chlamydia pneumoniae*), *Rickettsia* (for example, *Rickettsia ricketsii, Rickettsia prowazekii* or *Rickettsia akari*), brucella (for example, *Brucella abortus, Brucella melitensis*, or *Brucella suis*), *Proteus mirabilis, Serratia marcescens, Enterobacter clocae, Acetinobacter anitratus, Klebsiella pneumoniae* and *Francisella tularensis*. Preferably, the wound-specific bacteria is *staphylococcus, streptococcus, enterococcus, bacillus, Clostridium* species, *E. coli, yersinia, pseudomonas, Proteus mirabilis, Serratia marcescens, Enterobacter clocae, Acetinobacter anitratus, Klebsiella pneumoniae* or *Mycobacterium leprae*. For example, the wound-specific enzyme can be produced and/or secreted by *Staphylococcus aureus, Staphylococcus epidermidis, Streptococcus pyogenes, Pseudomonas aeruginosa, Enterococcus faecalis, Proteus mirabilis, Serratia marcescens, Enterobacter clocae, Acetinobacter anitratus, Klebsiella pneumoniae* and/or *Escherichia coli*.

As used herein, "modification" refers to alteration of a substrate, such as by cleavage or other directly or indirectly detectable means. The enzymes of the present invention can modify substrates, for example, proteins or polypeptides, by cleavage, and such modification can be detected to determine the presence or absence of a pathogen in a sample. One method for detecting modification of a substrate by an enzyme is to label the substrate with two different dyes, where one serves to quench fluorescence resonance energy transfer (FRET) to the other when the molecules, for example, dyes or colorimetric substances, are in close proximity, and is measured by fluorescence.

FRET is the process of a distance dependent excited state interaction in which the emission of one fluorescent molecule is coupled to the excitation of another. A typical acceptor and donor pair for resonance energy transfer consists of 4-[[-(dimethylamino)phenyl]azo]benzoic acid (DABCYL) and 5-[(2-aminoethylamino]naphthalene sulfonic acid (EDANS). EDANS is excited by illumination with 336 nm light, and emits a photon with wavelength 490 nm. If a DABCYL moiety is located within 20 angstroms of the EDANS, this photon will be efficiently absorbed. DABCYL and EDANS will be attached to opposite ends of a peptide substrate. If the substrate is intact. FRET will be very efficient. If the peptide has been cleaved by an enzyme, the two dyes will no longer be in close proximity and FRET will be inefficient. The cleavage reaction can be followed by observing either a decrease in DABCYL fluorescence or an increase in EDANS fluorescence (loss of quenching).

If the substrate to be modified is a protein, peptide, or polypeptide, the substrate can be produced using standard recombinant protein techniques (see for example, Ausubel et al., *Current Protocols in Molecular Biology*, John Wiley & Sons, (1998), the entire teachings of which are incorporated by reference herein). In addition, the enzymes of the present invention can also be generated using recombinant techniques. Through an ample supply of enzymes or their substrates, the exact site of modification can be determined.

The substrates are labeled with a detectable label that is used to monitor interactions between the enzyme and the substrate and detect any substrate modifications, for example, cleavage of the substrate or label resulting from such interactions. Examples of detectable labels include various dyes that can be incorporated into substrates, for example, those described herein, spin labels, antigen tags, epitope tags, haptens, enzyme labels, prosthetic groups, fluorescent materials, pH-sensitive materials, chemiluminescent materials, chromogenic dyes, colorimetric components, bioluminescent materials, and radioactive materials. Examples of suitable enzyme labels include horseradish peroxidase, alkaline phosphatase, β-galactosidase, and acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride and phycoerythrin; an example of a chemiluminescent material includes luminol; examples of bioluminescent materials include luciferase, luciferin, and aequorin, and examples of suitable radioactive material include $^{125}I$, $^{131}I$, $^{35}S$, and $^{3}H$. Other examples of detectable labels include Bodipy, Pyrene, Texas Red, IAEDANS, Dansyl Aziridine, IATR and fluorescein. Succimidyl esters, isothiocyanates, and iodoacetamides of these labels are also commercially available. In one embodiment, the substrate is labeled with a fluorescent probe and a quencher dye molecule.

The substrates can be labeled with at least one colorimetric component that is used to monitor interactions between the protein and the substrate and detect any substrate modifications, for example, cleavage of the peptide or label resulting from such interactions. In this way, the colorimetric component acts as a label or tag to indicate the presence or absence of the modification in order to reveal the presence or absence of a microorganism in a sample. In some embodiments the colorimetric component is covalently attached to the peptide.

In some embodiments the protein cleaves at least a portion of the substrate that includes a (at least one) colorimetric component. For example, if the substrate includes a blue colorimetric component and a yellow colorimetric component, the uncleaved substrate can appear green. After the protein cleaves a portion of the substrate that includes the yellow colorimetric component, the substrate can appear blue.

In some embodiments, the modification of the substrate includes hydrolyzing at least one peptide bond in the peptide and results in at least a portion of the peptide being cleaved from the substrate. The cleaved portion includes at least one colorimetric component, resulting in a visible color change. In other embodiments, the modification of substrate includes cleaving at least one colorimetric compound from the peptide, resulting in a visible color change.

The colorimetric component acts as a label or tag. In one embodiment, at least one colorimetric component is a different color from the other colorimetric component(s). Examples of colorimetric components include horseradish peroxidase, alkaline phosphatase, β-galactosidase, and acetylcholinesterase; examples of suitable prosthetic group complexes include streptavidin/biotin and avidin/biotin. In one embodiment of the invention, the substrate comprises a peptide with at least two colorimetric components, wherein each colorimetric component comprises a different color, and wherein the substrate is attached to a solid support. The modification of the substrate can comprise cleaving at least a portion of the substrate, wherein the portion includes one of the colorimetric components and the cleaving results in a visible color change.

The sample in which the presence or absence of bacteria is detected, or a wound infection is diagnosed, can be, for example, a wound (e.g., a wound surface on a subject), a body fluid, such as blood, urine, sputum, or wound fluid (for example, pus produced at a wound site). The sample or solid support can also be any article that bacteria may be contained on/in, for example, a catheter, a bag (e.g., a urine collection bag, a blood collection bag or a plasma collection bag), a disk, a polymer, a membrane, a resin, a glass, a sponge, an article that collects the sample, an article that contains the sample, a scope, a tilter, a lens, a foam, a cloth, a paper, a suture, a dipstick, a swab, a test tube, a well of a microplate, contact lens solutions, or a swab from an area of a room or building, for example, an examination room or operating room of a healthcare facility, a bathroom, a kitchen, or a process or manufacturing facility.

The present invention also features a biosensor for detecting a (one or more, for example, at least 2, at least 5, at least 10, at least 20, at least 30, at least 50, at least 75, or at least 100) wound pathogens, e.g., bacteria described herein and for notifying a consumer of the presence of the infection. The biosensor can be used in healthcare settings or home-use to detect infected wounds. It can comprise a (one or more) broad spectrum substrate(s) that is coupled to a solid support that is proximal to a wound or other body fluid that is being monitored for bacterial contamination. Preferably, the substrate is a synthetic serpin RSL domain peptide substrate covalently bound to a label and thus has a detection signal that upon proteolysis of the substrate-label bond indicates the presence of the bacteria.

The biosensor is made by first labeling a substrate of the invention, such as a synthetic serpin RSL domain peptide substrate, with one or more, and preferably, a plurality of detectable labels, for example, chromatogenic or fluorescent leaving groups. Most preferably, the labeling group provides a latent signal that is activated only when the signal is proteolytically detached from the substrate. Chromatogenic leaving groups include, for example, para-nitroanalide groups. Should the substrate come into contact with an enzyme secreted into a wound or other body fluid by bacteria or presented on the surface of a bacterial cell, the enzyme modifies the substrate in a manner that results in detection of such a modification, for example, a change in absorbance, which can be detected visually as a change in color (for example, on the solid support, such as a wound dressing), or using spectrophotometric techniques standard in the art.

The biosensor is a solid support, for example, a wound dressing (such as a bandage, or gauze), any material that is required to be sterile or free of microbial contamination (contaminants), for example, a polymer, a membrane, a resin, a glass, a sponge, a disk, a scope, a filter, a lens, a foam, a cloth, a paper, a dipstick or a sutures, or an article that contains or collects the sample (such as a container for holding bodily fluids, e.g., a urine collection bag, blood or plasma collection bag, test tube, catheter, swab, or well of a microplate).

Typically, the solid support is made from materials suitable for sterilization if the support directly contacts the wound or sample. In one embodiment of the present invention, the biosensor can be directly contacted with the wound. In some instances, a sterile covering or layer is used to prevent contamination of the wound or body fluid upon such direct contact. If such sterile coverings are used, they will have properties that make them suitable for sterilization, yet do not interfere with the enzyme/substrate interaction. Preferably, the portion of the biosensor that comes into contact with the wound is also non-adherent to permit easy removal of the biosensor from the sample surface. For example, if the biosensor comprises a wound dressing, the dressing contacts the wound for a time sufficient for the enzyme substrate to react and then the dressing is removed from the wound without causing further damage to the wound or surrounding tissue.

A broad spectrum substrate (e.g., a substrate suitable for detection of more than one pathogen or bacterium), suitably labeled with a detectable label, for example, a chromogenic dye, and attached or incorporated into a sensor apparatus, can act as an indicator of the presence or absence of multiple pathogenic bacteria that secrete the aforementioned enzymes.

The biosensor of the present invention also can optionally comprise one or more additional substrates (for example, at least 2, at least 5, at least 10, at least 20, at least 30, at least 50, at least 75, or at least 100 substrates) for produced and/or secreted enzymes of pathogenic bacteria. When more than one substrate is utilized, each may be labeled so as to distinguish it from another (for example, using different detectable labels) and/or each may be localized in a particular region on the solid support.

Substrates with hydrophobic leaving groups can be non-covalently bound to hydrophobic surfaces. Alternatively, hydrophilic or hydrophobic substrates can be coupled to surfaces by disulfide or primary amine, carboxyl or hydroxyl groups. Methods for coupling substrates to a solid support are known in the art. For example, fluorescent and chromogenic substrates can be coupled to solid substrates using non-essential reactive termini such as free amines, carboxylic acids or SH groups that do not effect the reaction with the wound pathogens. Free amines can be coupled to carboxyl groups on the substrate using, for example, a 10 fold molar excess of either N-ethyl-N'-(3-dimethylaminopropyl) carbodiimide hydrochloride (EDC) or N-cyclohexyl-N'-2-(4'-methyl-morpholinium) ethyl carbodiimide-p-toluene sulphonate (CMC) for 2 hrs at 4° C. in distilled water adjusted to pH 4.5 to stimulate the condensation reaction to form a peptide linkage. SH groups can be reduced with DTT or TCEP and then coupled to a free amino group on a surface with N-e-Maleimidocaproic acid (EMCA, Griffith et al., *Febs Lett.*, 134: 261-263 (1981), incorporated herein by reference).

The polypeptides of the invention can also comprise or consist of fragments and variants of the broad spectrum peptide substrates, e.g., serpin RSL domain peptide substrates, described herein. Variants include a substantially homologous polypeptide encoded by the same genetic locus as these peptide substrates, e.g., the α1 RSL domain in an organism, i.e., an allelic variant, as well as other variants. Variants also encompass polypeptides derived from other genetic loci in an organism, but having substantial homology to a peptide substrate described herein. Variants also include polypeptides substantially homologous or identical to these peptide substrates, but derived from another organism, i.e., an ortholog. Variants also include polypeptides that are substantially homologous or identical to these peptide substrates, that are produced by chemical synthesis. Variants also include polypeptides that are substantially homologous or identical to these peptide substrates, that are produced by recombinant methods.

The percent identity of two amino acid sequences can be determined by aligning the sequences for optimal comparison purposes (e.g., gaps can be introduced in the sequence of a first sequence). The amino acids at corresponding positions are then compared, and the percent identity between the two sequences is a function of the number of identical positions shared by the sequences (i.e., % identity=# of identical positions/total # of positions ×100). In certain embodiments, the length of the amino acid sequence aligned for comparison purposes is at least 30%, preferably, at least 40%, more preferably, at least 60%, and even more preferably, at least 70%, 80%, 90%, or 100% of the length of the peptide substrate sequence. e.g., the α1 RSL domain sequence. The actual comparison of the two sequences can be accomplished by well-known methods, for example, using a mathematical algorithm. A preferred, non-limiting example of such a mathematical algorithm is described in Karlin et al., *Proc. Natl. Acad. Sci. USA.* 90:5873-5877 (1993), which is incorporated herein by reference. Such an algorithm is incorporated into the BLAST programs (version 2.2) as described in Schaffer et al. (*Nucleic Acids Res.*, 29:2994-3005 (2001), incorporated herein by reference). When utilizing BLAST and Gapped BLAST programs, the default parameters of the respective programs can be used. In one embodiment, the database searched is a non-redundant (NR) database, and parameters for sequence comparison can be set at: no filters; Expect value of 10; Word Size of 3; the Matrix is BLOSUM62; and Gap Costs have an Existence of 11 and an Extension of 1.

In another embodiment, the percent identity between two amino acid sequences can be determined using the GAP program in the GCG software package (Accelrys Inc., San Diego, Calif.) using either a Blossom 63 matrix or a PAM250 matrix, and a gap weight of 12, 10, 8, 6, or 4 and a length weight of 2, 3, or 4. In yet another embodiment, the percent identity between two nucleic acid sequences can be accomplished using the GAP program in the GCG software package (Accelrys Inc.), using a gap weight of 50 and a length weight of 3.

Other preferred sequence comparison methods are described herein.

The invention also encompasses polypeptide substrates having a lower degree of identity but having sufficient similarity so as to perform one or more of the same functions performed by the peptide substrate, e.g., the ability to act as a substrate for enzymes produced or secreted by bacteria, for example, wound-specific bacteria. Similarity is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science.* 247: 1306-1310 (1990), incorporated herein by reference).

Functional variants can also contain substitution of amino acids similar to those in the α1 RSL domain that result in no change or an insignificant change in function. Alternatively, such substitutions may positively or negatively affect function to some degree. Non-functional variants typically contain one or more non-conservative amino acid substitutions, deletions, insertions, inversions, or truncation or a substitution, insertion, inversion, or deletion in a critical residue or critical region, such critical regions include the proteolytic cleavage site for an infection-specific protease.

Amino acids in a peptide substrate of the present invention that are essential for cleavage by an enzyme, e.g., a protease, can be identified by methods known in the art, such as site-directed mutagenesis or alanine-scanning mutagenesis (Cunningham et al., *Science*, 244: 1081-1085 (1989), incorporated herein by reference). The latter procedure introduces a single alanine mutation at each of the residues in the molecule (one mutation per molecule).

The invention also includes polypeptide fragments of the peptide substrates or functional variants thereof, including biologically active fragments with 60%, 70%, 80%, 90% or 95% sequence homology to a synthetic or naturally-occurring peptide substrate described herein, e.g., the α1 RSL domain sequence. The present invention also encompasses fragments of the variants of the polypeptides described herein. Biologically active fragments include fragments that have retain the ability to act as substrates for enzymes produced or secreted by bacteria, for example, wound-specific bacteria Fragments can be discrete (not fused to other amino acids or polypeptides) or can be within a larger polypeptide. Further, several fragments can be comprised within a single larger polypeptide. In one embodiment a fragment designed for expression in a host can have heterologous pre- and pro-polypeptide regions fused to the amino terminus of the polypeptide fragment and an additional region fused to the carboxyl terminus of the fragment.

The biosensors and peptides of the present invention can be used in any situation where it is desirable to detect the presence or absence of bacteria, and in particular, pathogenic bacteria. For example, bacteria that collects on work surfaces in health care facilities, and in particular in operating rooms can be detected with a biosensor as described herein. A substrate, or more than one substrate, that can be modified by an enzyme secreted by or presented on the surface of a bacteria is labeled and covalently bound to a collector substrate, such as cotton fibers on the tip of a swab. When more than one substrate is utilized, each may be labeled so as to distinguish it from another (for example, using different detectable labels) and/or each may be localized in a particular region on the solid support. The swab tip is used to wipe the surface suspected of being contaminated by bacteria. The swab tip is placed in a medium and incubated using conditions that allow modification of the labeled substrate if an enzyme specific for the bound, labeled substrate(s) is present.

The present invention also features a kit for detecting wound-specific bacteria as described herein. The kit can comprise a solid support, for example, having a plurality of wells (e.g., a microtiter plate), to which a detectably labeled substrate (such as a serpin reactive site loop (RSL) domain peptide substrate) is linked, coupled, or attached. A means for providing one or more buffer solutions is provided. A negative control and/or a positive control can also be provided. Suitable controls can easily be derived by one of skill in the art. A sample suspected of being contaminated by a pathogen (e.g., a bacterium described herein) is prepared using the buffer solution(s). An aliquot of the sample, negative control, and positive control is placed in its own well and allowed to react. Those wells where modification of the substrate, for example, a color change, is observed are determined to contain a microbial pathogen. Such a kit is particularly useful for detecting a wound infection in a subject.

Also encompassed by the present invention is a kit that comprises a biosensor, such as a packaged sterilized wound dressing, and any additional reagents necessary to perform the detection assay.

EXAMPLES

The present invention will now be illustrated by the following Examples, which are not intended to be limiting in any way.

Example 1

Preparation of Bacteria for Detection of the Absence or Presence of Bacteria in a Sample A culture of each of the following bacterial species was grown overnight (O/N) in Brain Heart Infusion (BHI) broth at 37° C. with vigorous shaking (~200 rpm), using methods that are standard in the art: *Staphylococcus aureus; Streptococcus pyogenes; Serratia marcescens; Escherichia coli; Pseudomonas aeruginosa* (PA14); *Pseudomonas aeruginosa* (GSU3); and *Enterococcus faecalis*. After overnight growth, a 1 ml sample of each culture was obtained, and the cells were removed from the culture supernatant by centrifugation at 12,000×g for 5 minutes. The remaining culture supernatants were stored on ice until required (less than one hour). The bacteria were assayed for the presence or absence of enzymes as described below.

Alternatively, the bacterial cells are not separated from the culture supernatant, but rather, the assay is carried out on a sample containing the cells still in suspension in their culture broth. After 48 hours (two days) of growth, the procedure was repeated.

Example 2

Extraction of Bacteria from Wound Dressings for Determining the Absence or Presence of Bacteria in a Wound Sample Thirty-five fresh, frozen wound dressings were obtained from Dr. Thomas Serena, medical director of the St. Vincent Wound Clinic, Erie, Pa., and founder of the Penn North Centers for Advanced Wound Care. The dressings were classified as medical waste for this study and no information on the wounds or the patients was obtained. The dressings were from random wounds and were collected and shipped on the same day. The dressings were shipped on dry ice and stored immediately at −80° C. upon arrival.

Extraction

On the day of analysis, the dressings were removed from the freezer and defrosted enough to stretch out the dressings for cutting. All work was done under sterile conditions and following the Blood-Borne Pathogen Guidelines. A wide variety of dressing sizes and exudates were represented. Most of the dressings were gauze-type with some including an absorbent center (i.e., it appeared that no hydrocolloid or advanced wound management dressings were included). A 2×3.5 cm rectangle was cut from each dressing (7 cm$^2$ area). The most representative portion of the dressing was chosen in the case of large dressings.

A wide variety of dressing colors and exudates were obtained. The dressings were placed in 15 ml sterile conical tubes with 3 ml of sterile PBS and the extraction was performed overnight at 4° C. There were several samples that turned the PBS cloudy white immediately upon immersion of the dressing (Samples 2, 3, 9, 14, 22, 26, and 27). We suspect that these dressing samples contained silver from treatment of the wounds. After the dressing extraction, the color of each of the solutions was recorded. Three 0.5 ml aliquots of each extract were collected for storage and testing.

Figure 10A:
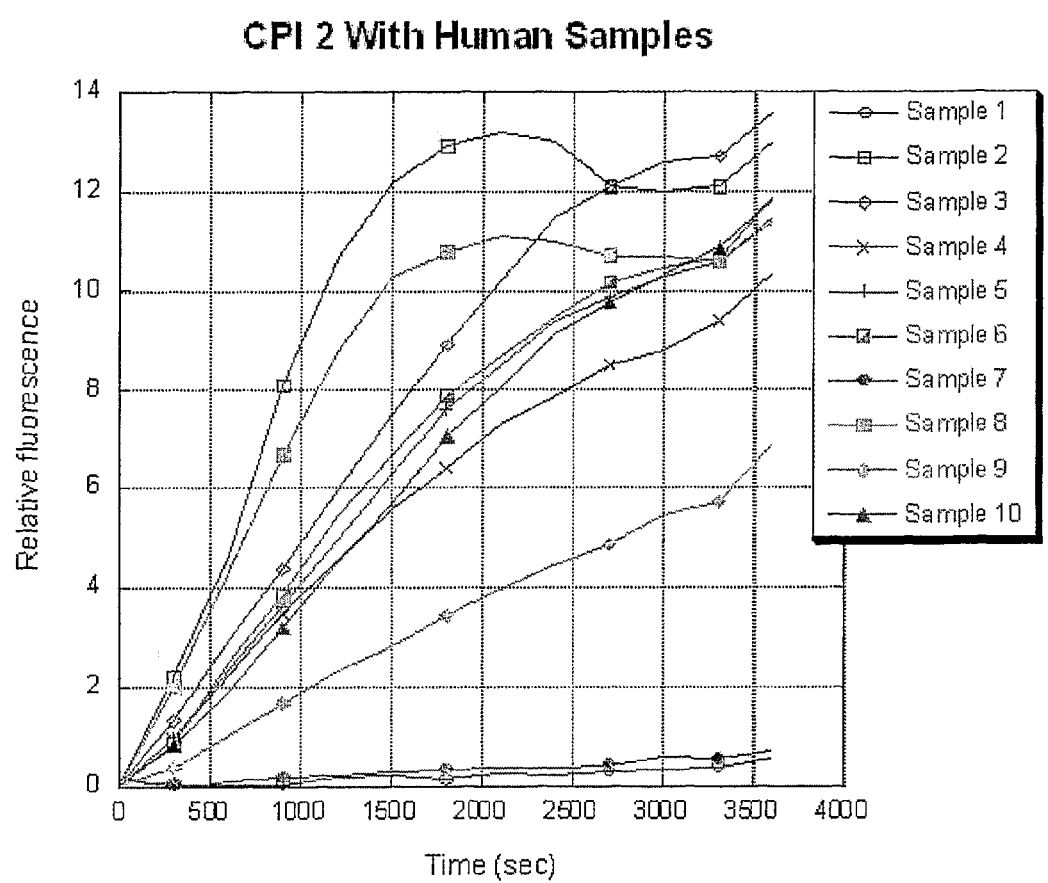
FIGS. 10A through 10D are graphs illustrating the relative fluorescence of bacteria extracted from wound dressings (peptide substrate: CPI2) (reaction buffer: 1×PBS). (A: wound sample nos. 1-10; B: wound sample nos. 11-20; C: wound sample nos. 20-30; D: wound sample nos. 31-35).
Figure 10B:
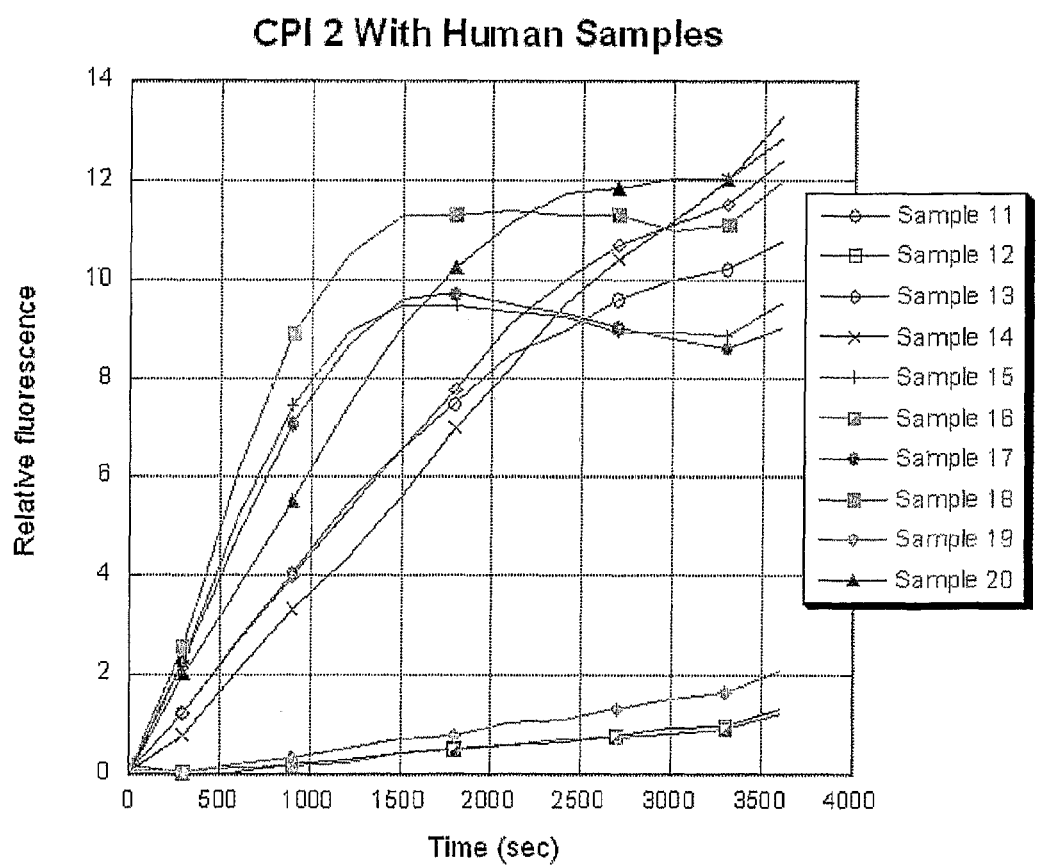
Figure 10C:
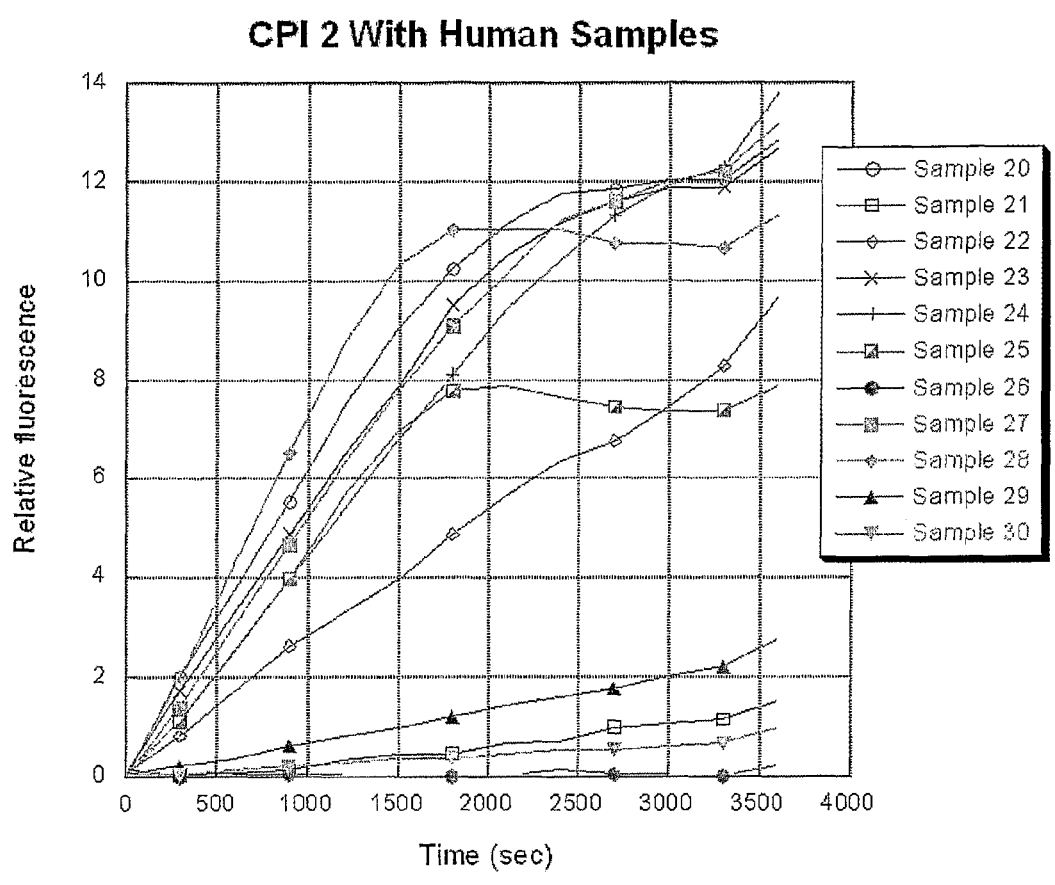
Figure 10D:
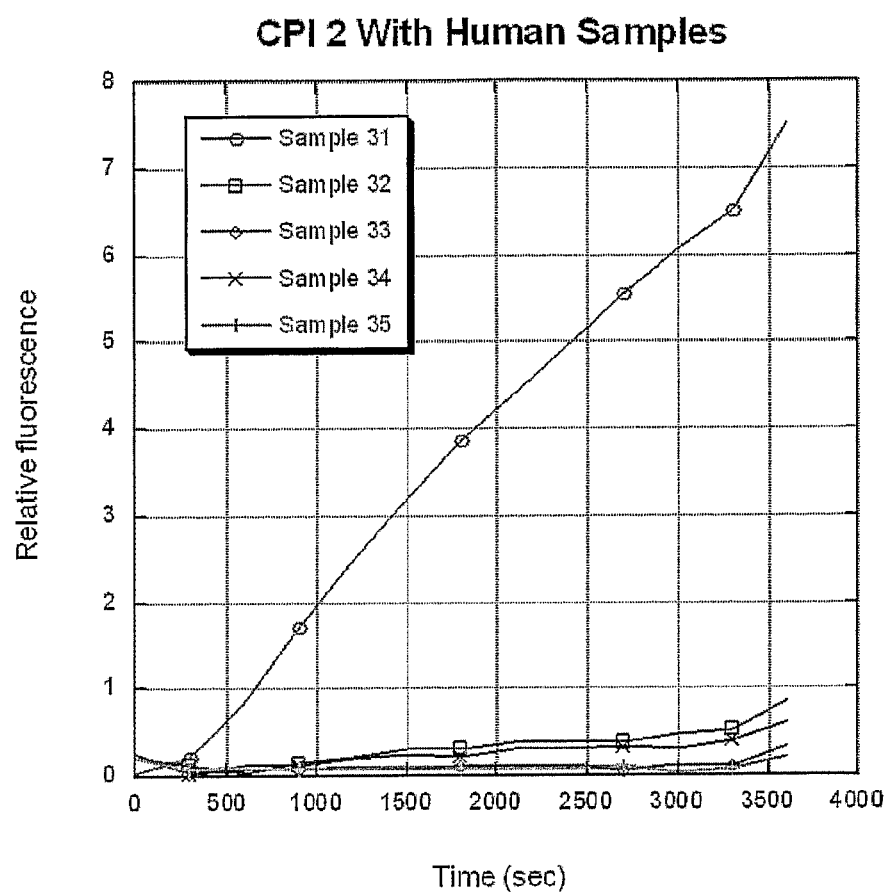

The cleavage reaction was carried out with 10 μl of wound sample extract, 3 μl of CPI2 peptide substrate (5 mg/mL in water/DMSO) in 100 μl total volume at 37° C. The reaction was followed on a fluorimetric plate reader using an excitation wavelength of 355 nm and an emission wavelength of 485 mn (FIGS. 10A-0D).

Example 3

Broad Spectrum Assay Using Variants of α1-PI RSL Sequence

Two peptide substrates, CPI1 and CPI2, were designed to encompass all of the cleavage sites of the RSL sequence, as shown in FIGS. 1A and 1B. The peptide substrates were labeled with the fluorescent probe edans (5-((2-aminoethyl)amino)naphthalene-1-sulfonic acid) and the quencher dye molecule dabcyl ((4-(4-(dimethylamino)phenyl)azo)benzoic acid).

```
                                              (SEQ ID NO: 1)
(CPI1)  Edans-EAAGAMFLEAIPK-Dabcyl (SEQ ID NO: 2)
(CPI2)  Edans-EGAMFLEAIPMSIPK-Dabcyl
```

The bacteria were grown in an incubator overnight at 37° C. in 5 mL BHI (Brain Heart Infusion) media. Each of the resulting cultures was split into two samples. One was used as a culture, and the other was spun down by centrifugation and the supernatant was collected. The assays were run in 20 mM tris buffer (pH 7.2) with 150 mM NaCl added (PBS). The cleavage reaction was carried out with 7 μL of culture or supernatant and 3 μL of peptide substrate (5 mg/mL in water/DMSO) in 100 μL total volume at 37° C. The reaction was followed on a fluorimetric plate reader using an excitation wavelength of 355 nm and an emission wavelength of 485 nm.

Figure 2A:
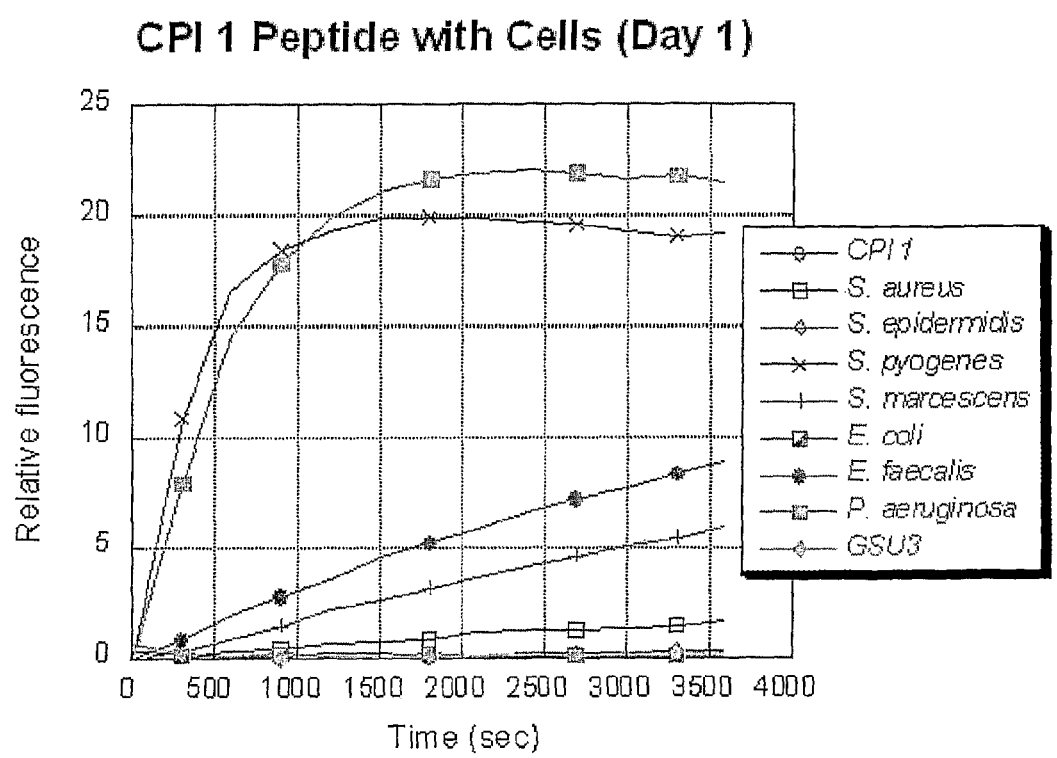
FIGS. 2A through 2D.
Figure 2B:
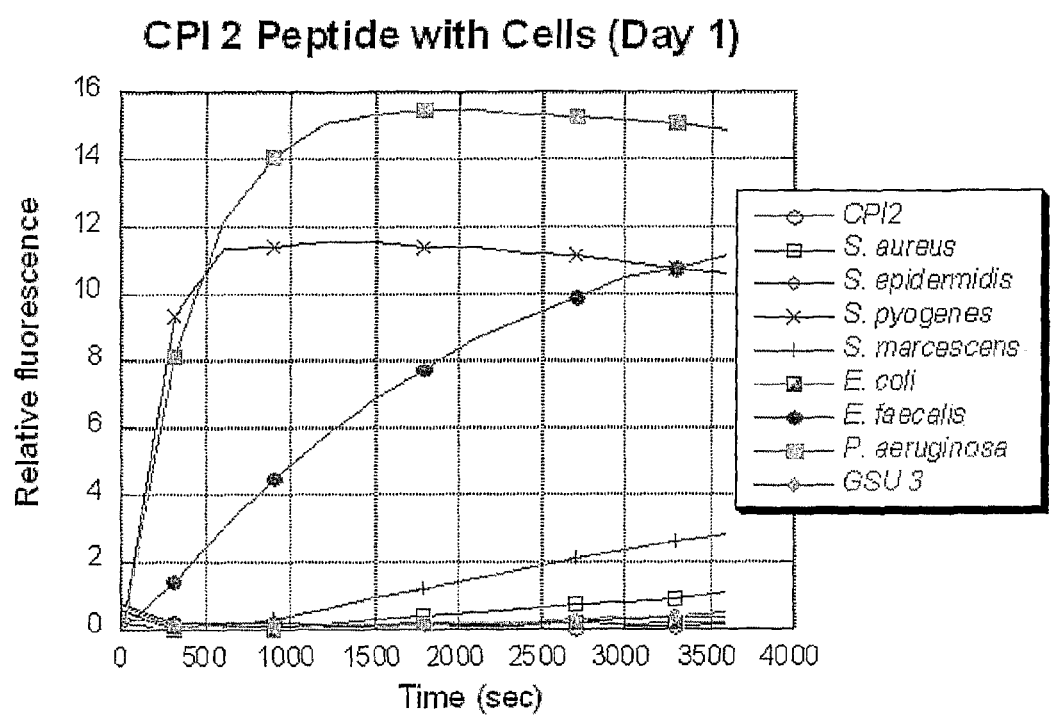

The first set of experiments was performed by addition of the bacterial culture (media and cells) directly into the assay solution. The first assay used overnight (one day) growth cells and supernatants and peptides CPI1 and CPI2 as substrates. As shown in FIGS. 2A and 2B, protease activity was observed for a number of the bacteria with the peptide substrates.

Figure 2C:
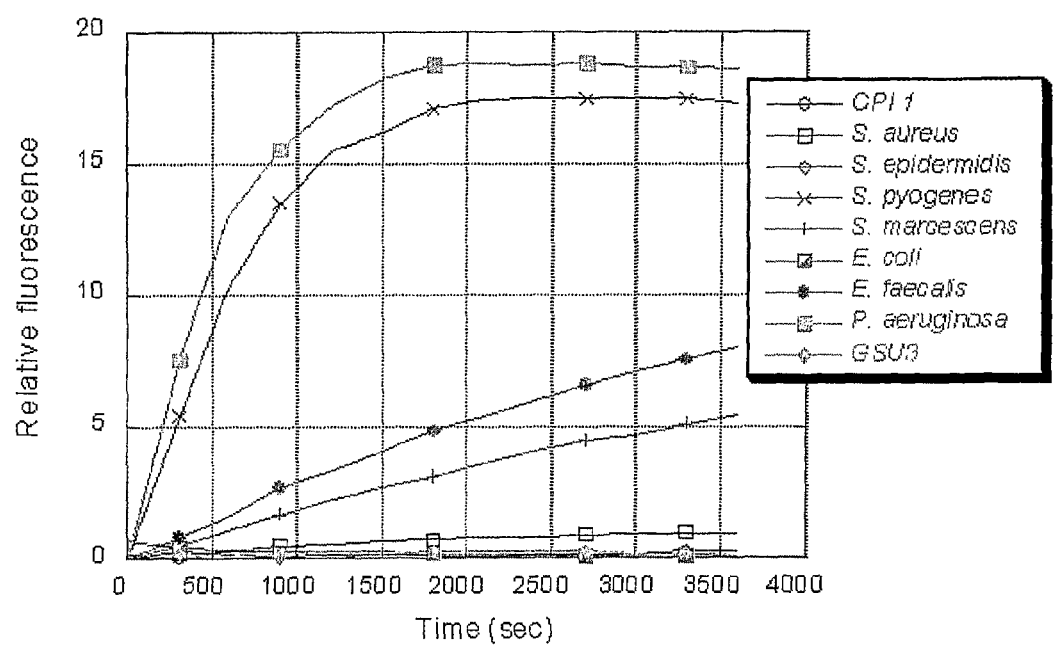
Figure 2D:
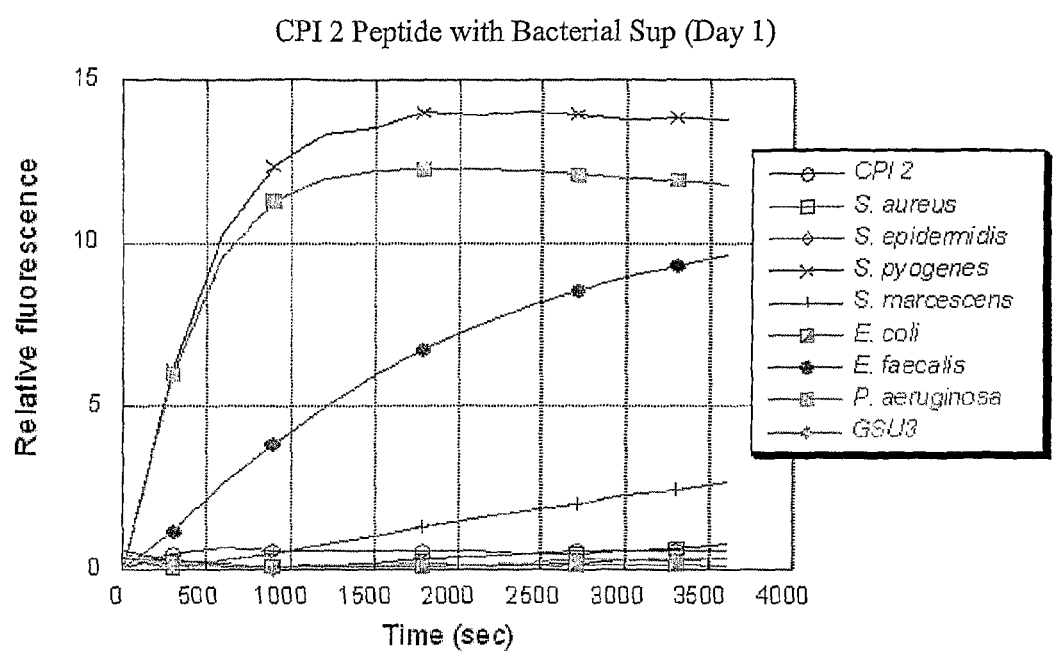
Figure 3A:
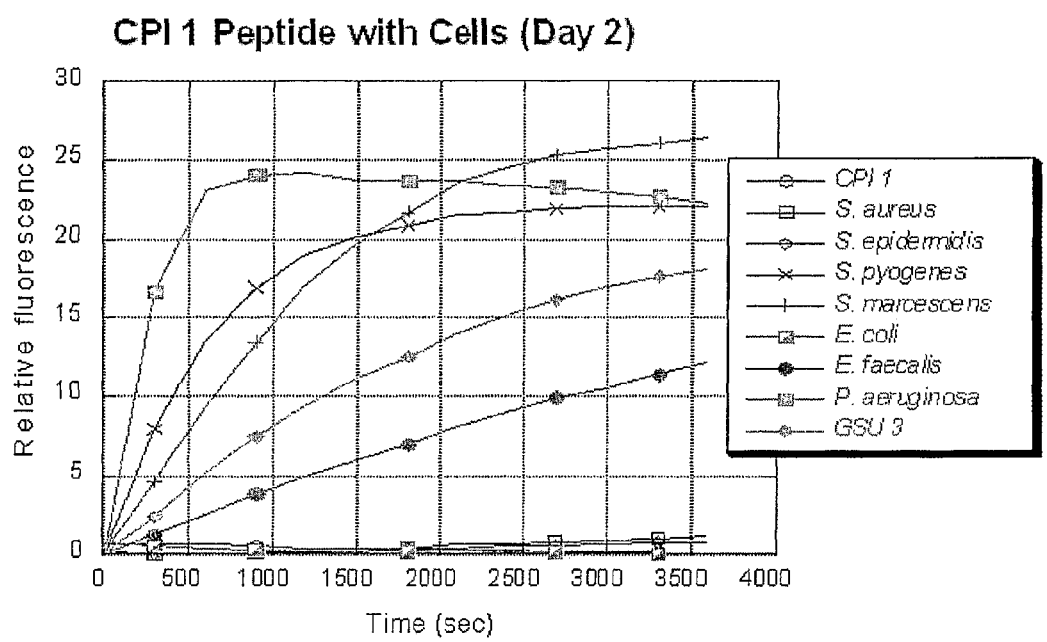
FIGS. 3A through 3D.
Figure 3B:
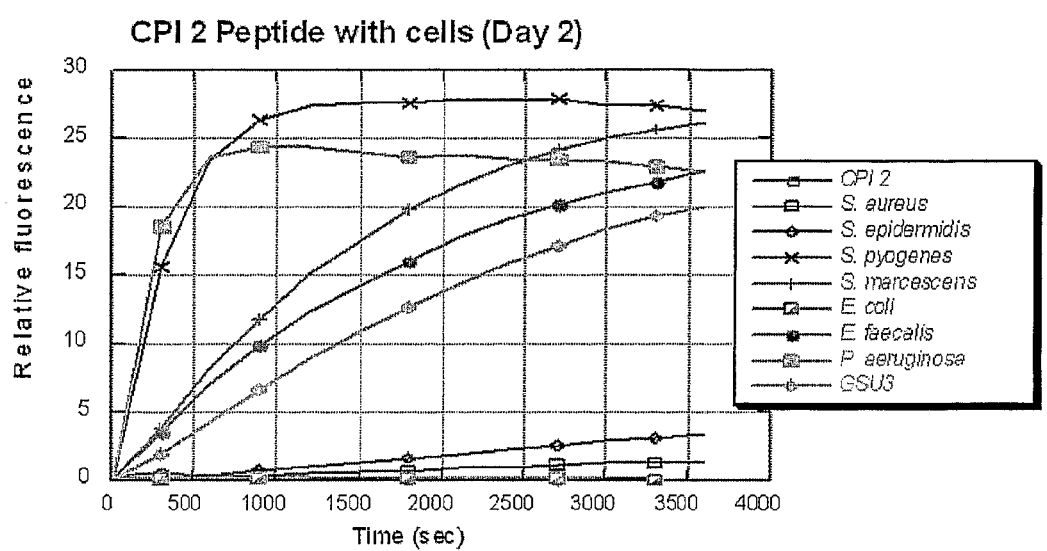
Figure 3C:
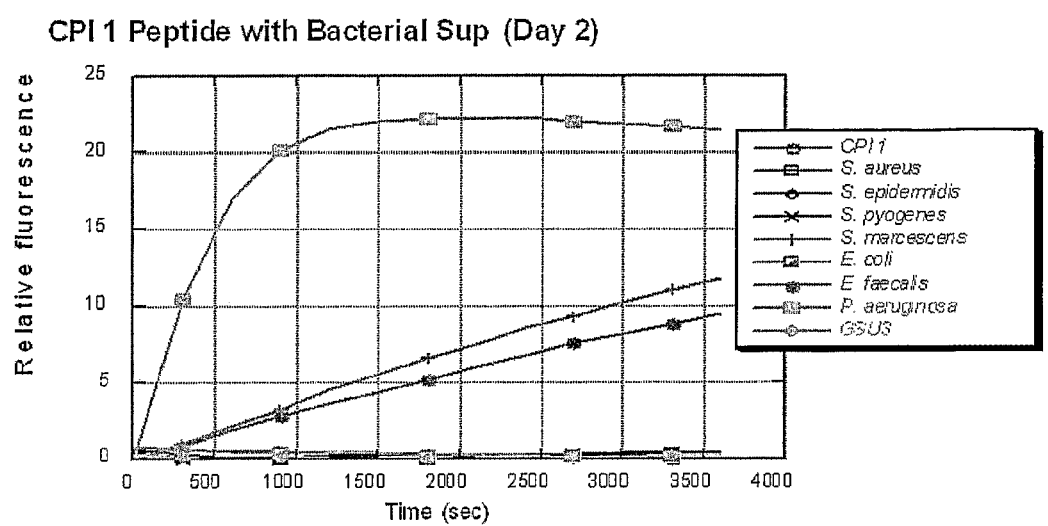
Figure 3D:
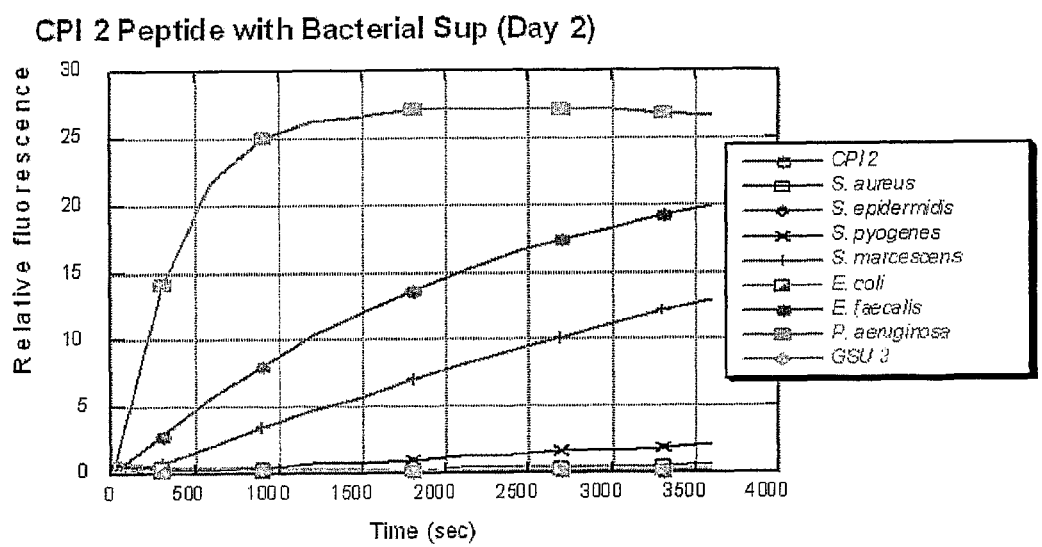

To determine which of the bacteria have secreted proteases, a similar experiment was performed using bacterial supernatants obtained from the overnight grown bacterial cultures with the peptides CPI1 and CPI2. As shown in FIGS. 2C and 2D, the results were similar to those bacterial culture, indicating that the proteases are secreted.

In a second set of experiments, a similar assay was performed using 48 hour (two day) growth cells and supernatants. The assay used CPI1 and CPI2 as substrates. The assay was performed as previously described for the first set of experiments, with the exception of using 5 μl of bacterial supernatant. The results are shown in FIGS. 3A-D.

Example 4

Development of Biosensor Surfaces

The attachment of molecules to surfaces can be performed by the use of several different types of interactions. Typically, proteins can be attached to surfaces using hydrophobic, electrostatic, or covalent interactions. There are many commercially available membranes and resins with a variety of surface properties. Surfaces can also be chemically modified to provide the required surface properties.

Commercially available transfer membranes exist for protein and peptide binding. They consist of positively and negatively charged polymers such as ion exchange membrane disc filters and resins. Nitrocellulose membranes offer hydrophobic and electrostatic interactions. Glass fiber membranes offer a hydrophobic surface that can easily be chemically modified to add functional groups. There are also modified polymer membranes that offer reactive functional groups that covalently bind proteins and peptides.

It is also possible to utilize various functional groups on membranes or resins and a crosslinking agent to covalently link to proteins. Crosslinking reagents contain two reactive groups thereby providing a means of covalently linking two target functional groups. The most common functional groups to target on proteins are amine, thiol, carboxylic acid, and alcohol groups that are used to form intramolecular crosslinks. Crosslinking agents can be homobifunctional or heterobifunctional and a selection of crosslinking agents of various lengths are commercially available.

Metal chelate (affinity binding) interactions can provide a stronger bond to biological molecules. A his-tag built into the peptide substrate can be used to allow linkage to a nickel binding resin. Histidine-tagged peptides are purified based on the ability of consecutive histidine residues to bind to a resin (Sepharose) containing nickel ions immobilized by covalently attached nitrilotriacetic add (NTA). A CPI3 peptide comprising CGAMFLEAIPMSIPAAAHHHHH (SEQ ID NO:5) was made based on CPI2 with the addition of a histidine tag, CPI3 was labeled at the cysteine group with a colorimetric dye. In this example, a remazol dye, Reactive Black 5 (RB5), was used. This dye produces a dark blue color with a peak absorption at 595 nm.

(SEQ ID NO: 5)
CPI3 [Ac]-CGAMFLEAIPMSIPAAAAHHHHH-[OH]
         |
         RB5

The CPI3-Reactive Black 5 labeled peptide was bound to a NTA resin through the histidine tag. The NTA resin gave a high level of peptide binding without non-specific binding.

Labeled CPI3 on NTA resin was cleaved overnight at 37° C. with *Pseudomonas aeruginosa* (PA14). Cleaved peptide was collected with a positively charged membrane (Pall SB6407) placed in the tube with the resin and bacteria. A control sample consisted of CPI3 on NTA resin with a positively charged membrane in phosphate buffered saline (PBS). A strong color change was obtained on the positively charged membrane in the sample with bacteria when compared to the control as shown in. The color change on the membrane indicated that the CPI3 was cleaved and the cleaved portion with dye has diffused onto the membrane creating a blue color.

Lysine peptide tags can be used to link to a surface such as UltraBind™ (Pall Gelman Laboratory, Ann Arbor, Mich.). UltraBind is a polyethersulfone membrane that is modified with aldehyde groups for covalent binding of proteins. Proteins are directly reacted with the UltraBind surface. It is also possible to link proteins or peptides to the surface using cross linker chains. For example, the carbodiimide, EDC (1-ethyl-3-(3-dimethylaminopropyl)carbodiimide, hydrochloride) is commonly used to link carboxylic acid groups to amines. The lining of the peptide with a cross linking agent allows the choice of a linker chain to extend the peptide off the surface of the membrane while still covalently binding it. The linking of the peptide through a cross linker can be optimized to make the peptide available to the bacterial enzymes. This allows for optimization of the reaction time of the sensor since peptide availability is directly related to this parameter.

Example 5

Surface Sensor Sensitivity

CPI2 was determined to be a good candidate for a broad-spectrum sensor. Surface sensors were constructed as follows:
Membrane Used: Pall SB6407
Peptide Used: CPI2
Amount Used: 8 µg
The sensors were air dried and stored overnight at −20° C. Sensors were loaded into sterile 96 well plates for the sensitivity study.

The bacteria *E. faecalis, P. aeruginosa, S. aureus, S. pyogenes,* and *S. marcescens* were grown in an incubator overnight at 37° C. in 5 ml BHI (Brain Heart Infusion) media and diluted to the concentrations given for each experiment. Each strain of bacteria was diluted with PBS (pH 7.4) to obtain an optical density (OD) of approximately 0.52 at 550 nm. This OD was assumed to represent approximately $10^4$ cells/ml of bacteria. The $10^8$ cells/ml stock of each bacteria was diluted with PBS to obtain a concentration series of: $10^7, 10^6, 10^5$ and $10^4$ cells/ml. Sensitivity testing consisted of placing 100. µgL of each of the concentration series of $10^7, 10^6, 10^5$ and $10^4$ cells/ml (cells) onto a row of sensors. Controls for each sensitivity testing consisted of sensors exposed to 100 µL PBS.

Data was taken at 4, 24 and 48 hours for each plate. Data consisted of color (fluorescent) images of each plate taken under relatively uniform conditions (lighting, exposure time, etc.) using a Kodak DC290 digital camera. Images were analyzed using NIH ImageJ, a public domain image processing and analysis program developed at the National Institutes of Health (NIH). Analysis consisted of measuring the intensity value within each well (i.e., the sum of the intensity values of all the pixels in the selection divided by the number of pixels). Pixels range in value from 0 to 1. ImageJ displays zero as white and those with a value of 1 as black. All sensor sensitivity data is plotted on an index scale from 0 to 1 versus time and the trends accurately reflect what is seen in the images.

Figure 4A:
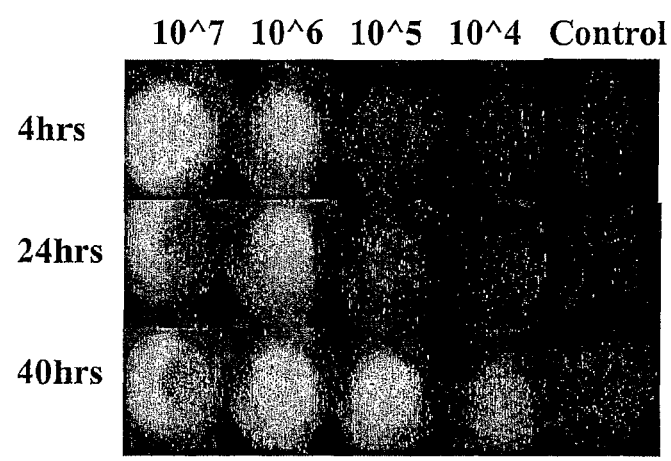
FIGS. 4A and 4B illustrate sensor data for *E. faecalis* (with a concentration series of: $10^7$, $10^6$, $10^5$ and $10^4$ cells/ml) with CPI2 peptide.
Figure 4B:
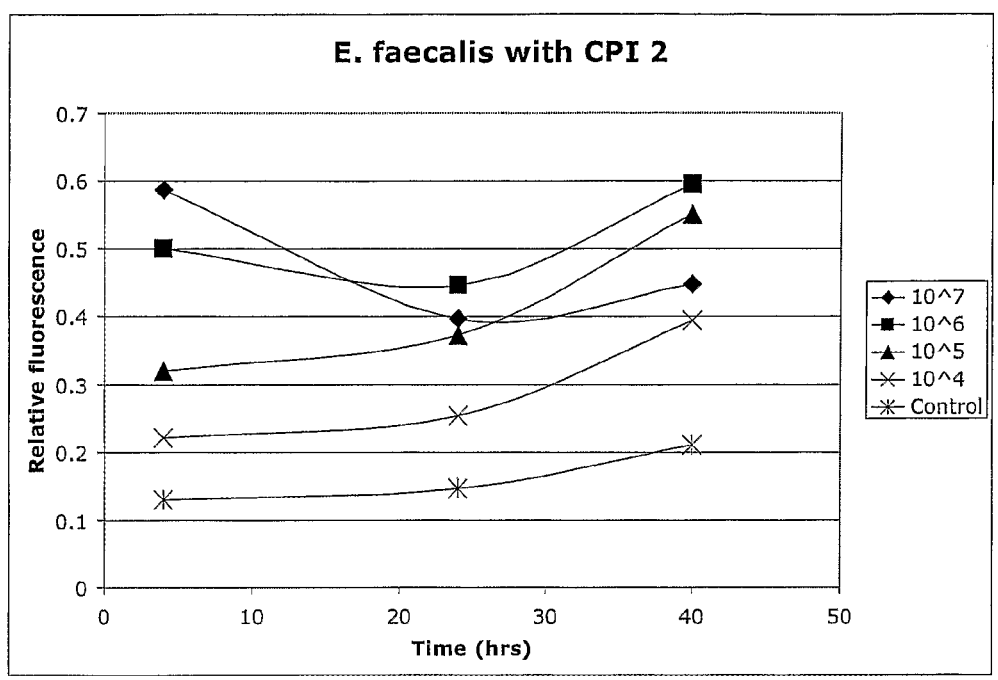

The results for the *E. faecalis* sensor tested with a concentration series of: $10^7, 10^6, 10^5$, and $10^4$ cells/ml are shown in FIGS. 4A and 4B.

Figure 5A:
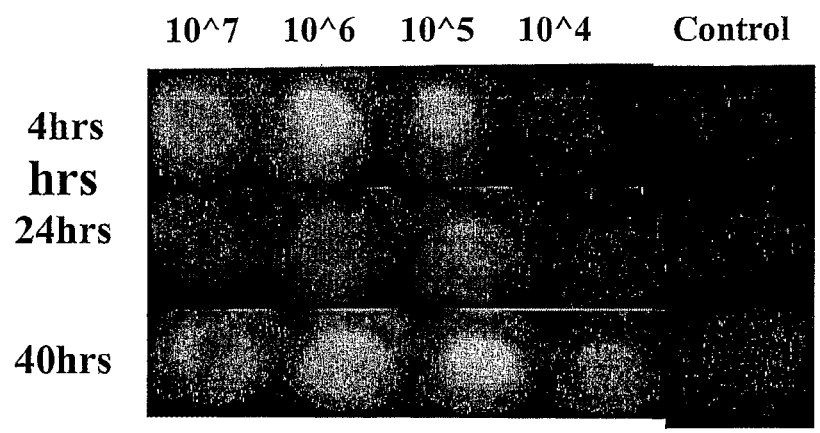
FIGS. 5A and 5B illustrate sensor data for *P. aeruginosa* (with a concentration series of: $10^7$, $10^6$, $10^5$ and $10^4$ cells/ml) with CPI2 peptide. Figure SA shows images of sensors incubated with bacteria under 365 nm UV light source.
Figure 5B:
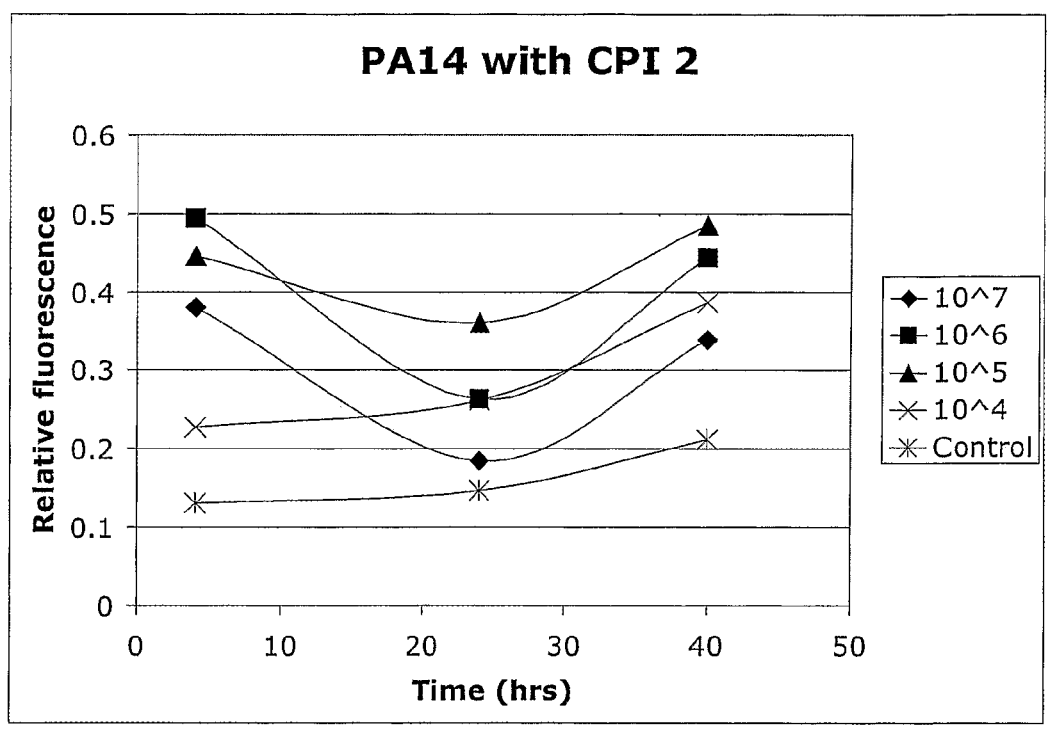

The results for the *P. aeruginosa* sensor tested with a concentration series of: $10^7, 10^6, 10^5$, and $10^4$ cells/ml are shown in FIGS. 5A and 5B.

Figure 6A:
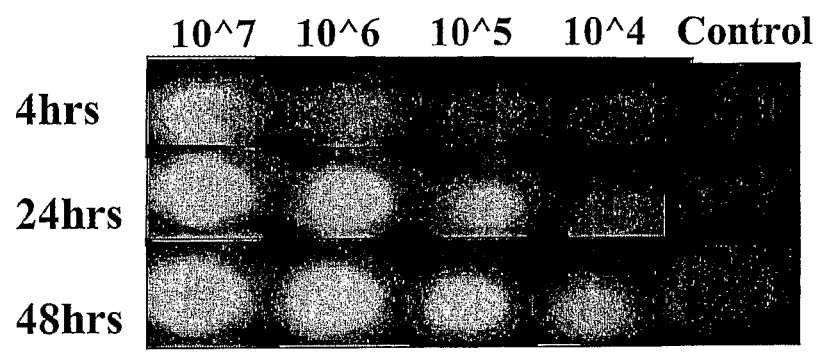
FIGS. 6A and 6B illustrate sensor data for *S. aureus* (with a concentration series of: $10^7$, $10^6$, $10^5$ and $10^4$ cells/ml) with CPI2 peptide.
Figure 6B:
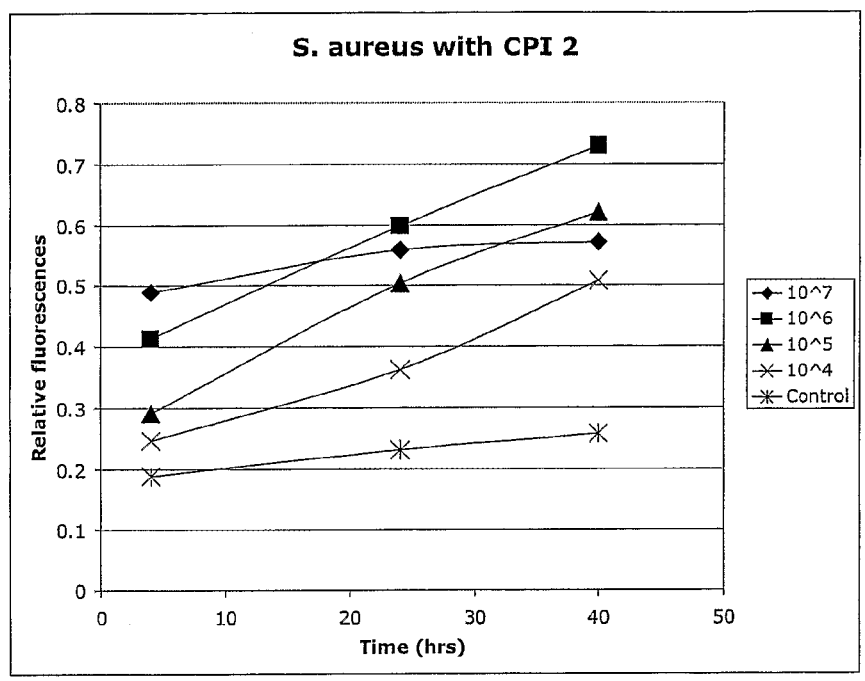

The results for the *S. aureus* sensor tested with a concentration series of: $10^7, 10^6, 10^5$, and $10^4$ cells/ml are shown in FIGS. 6A and 6B.

Figure 7A:
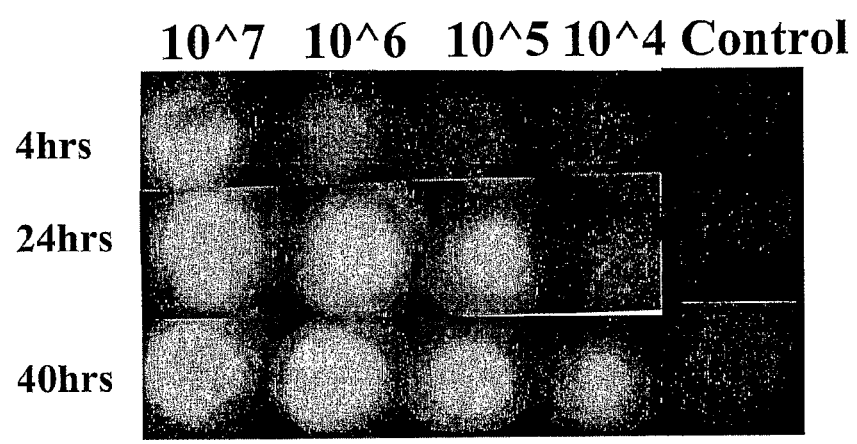
FIGS. 7A and 7B illustrate sensor data for *S. pyogenes* (with a concentration series of: $10^7$, $10^6$, $10^5$ and $10^4$ cells/ml) with CPI2 peptide.
Figure 7B:
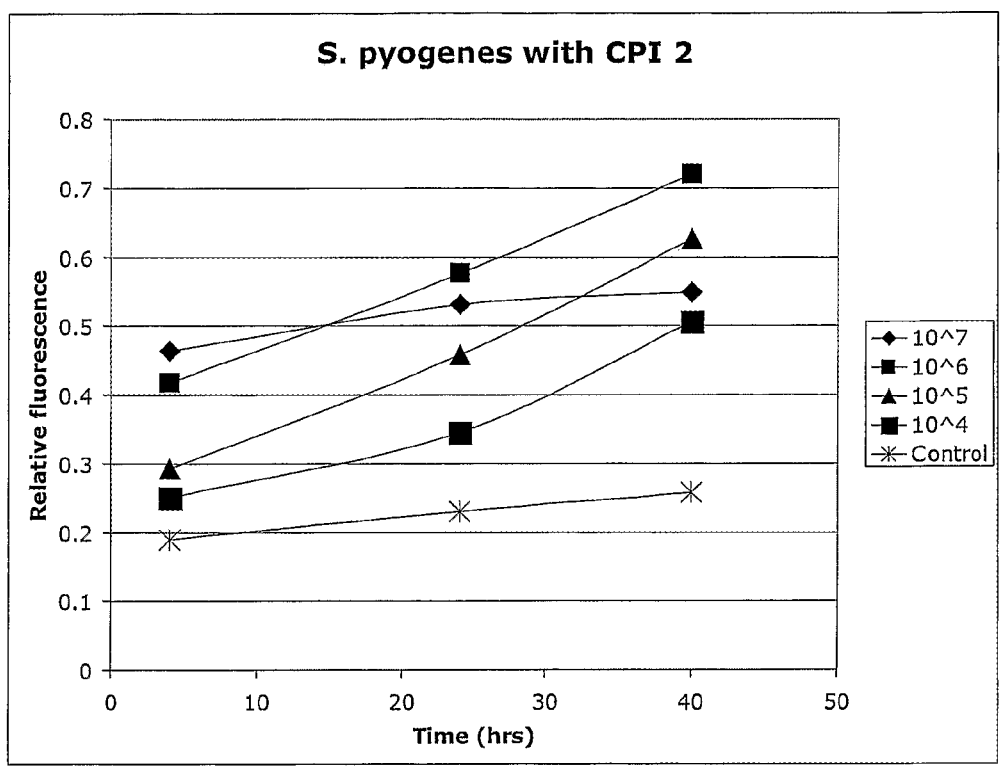

The results for the *S. pyogenes* sensor tested with a concentration series of: $10^7, 10^6, 10^5$, and $10^4$ cells/ml are shown in FIGS. 7A and 7B.

Figure 8A:
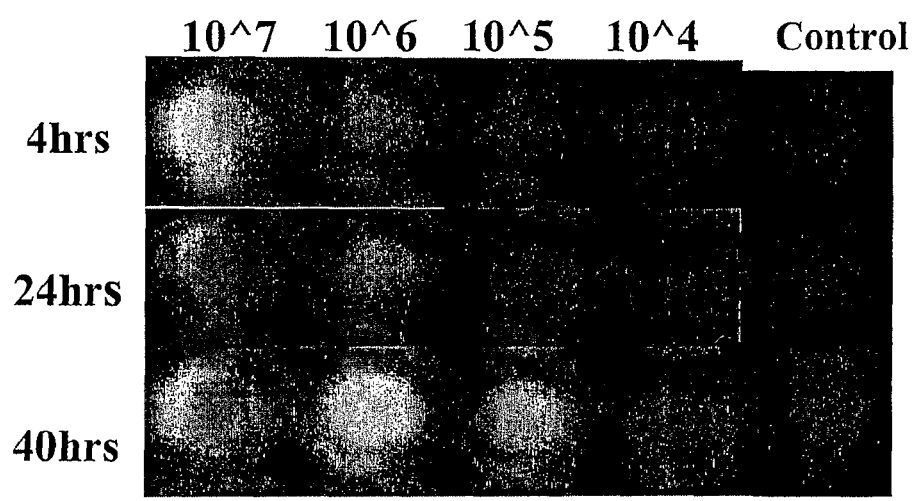
FIGS. 8A and 8B illustrate sensor data for *S. marcescens* (with a concentration series of: $10^7$, $10^6$, $10^5$ and $10^4$ cells/ml) with CPI2 peptide.
Figure 8B:
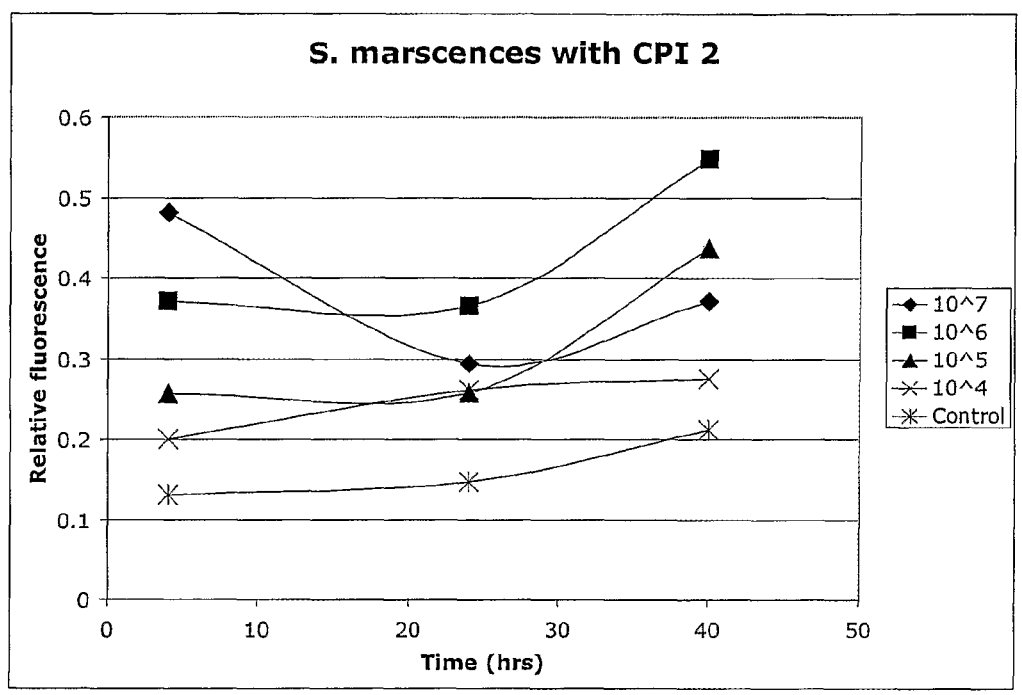

The results for the *S. marcescens* sensor tested with a concentration series of: $10^7, 10^6, 10^5$, and $10^4$ cells/ml are shown in FIGS. 8A and 8B.

The CPI2 peptide substrate was efficiently cleaved by the proteases of *Enterococcus, Pseudomonas, Staphylococcus, Streptococcus,* and *Serratia*. CPI2 peptide substrate was not cleaved when incubated with *E. coli* cells or supernatant. CPI2 peptide was not cleaved in the presence of uninfected wound fluid. At the highest concentrations of bacteria, many of the fluorescence assays above show quenching which is evidenced by a drop in the fluorescence level for some of the $10^7$ and $10^6$ samples. The assay can be repeated with less substrate on the membrane to reduce the fluorescence quenching.

Figure 9A:
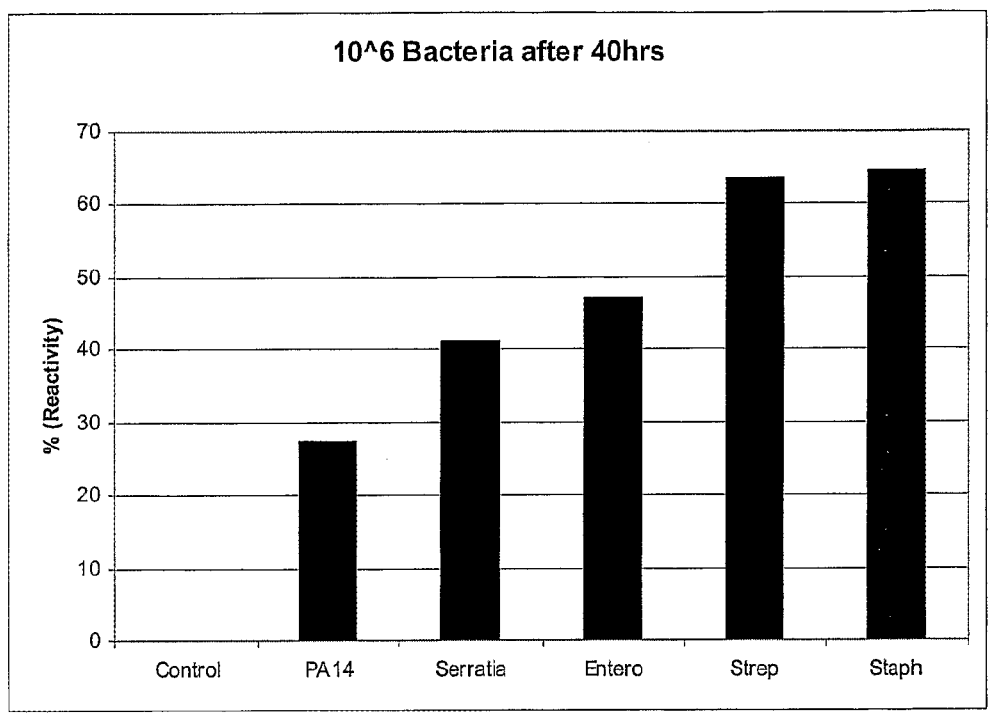
FIGS. 9A through 9C are bar graphs illustrating the relative incubation for 40 hours with differing concentrations of bacteria. (A=$10^6$ CFU; B=$10^5$ CFU; C=$10^4$ CFU) (Staph=*Saphylococcus aureus*; Serratia=*Serratia marcescens*; Strep=*Streptococcus salivarius*; PA14=*Pseudomonas aeruginosa*; Entero=*Enterococcus faecalis*).
Figure 9B:
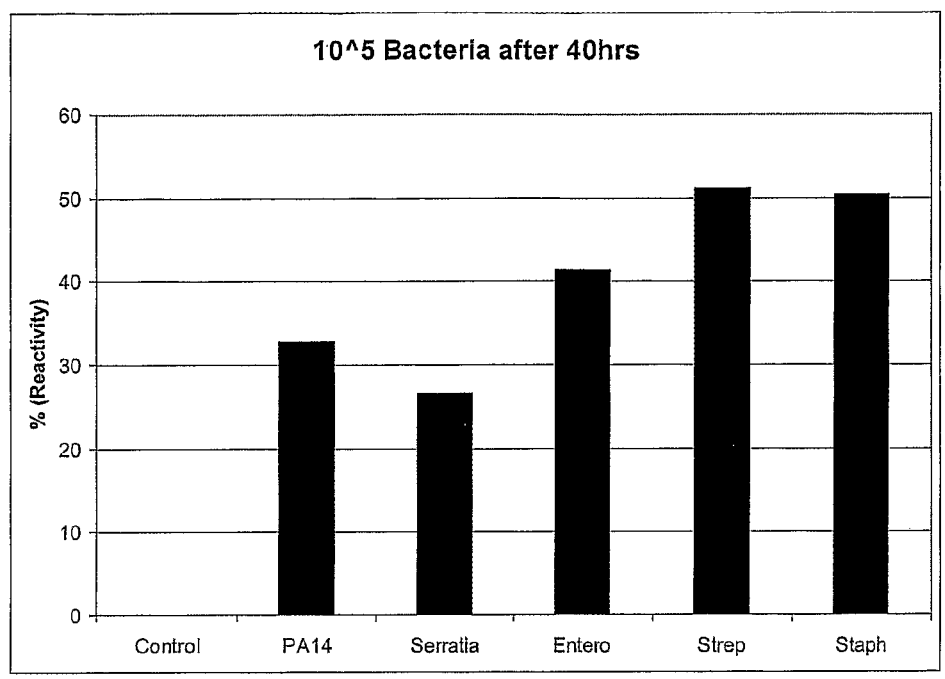
Figure 9C:
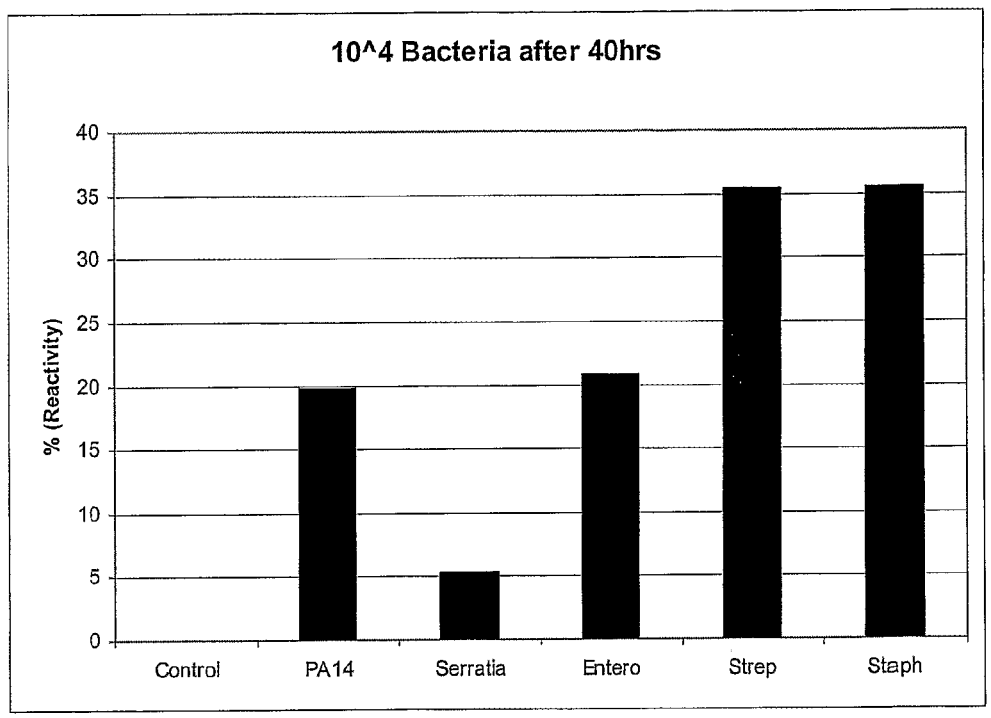

The reactivity of each sensor was compared at the end of the sensor study (40 hours) to determine the relative signal obtained from each. The results are shown in FIGS. 9A-9C. The CPI2 peptide was efficient in detecting most pathogens at $10^5$ CFU. All five bacteria (but not *E. coli*) give a strong signal at a concentration of $10^5$ bacteria/ml. However, at a concentration of $10^4$ bacteria/ml, *Serratia* is not observed to give a signal that can be significantly measured above the background.

The cross reactivity of the CPI2 peptide with harmless bacteria and with wound fluid can be analyzed more thoroughly using appropriate controls. The applicability of the CPI2 peptide substrate on a wound dressing and in a in vive pig study can also be determined.

While this invention has been particularly shown and described with references to preferred embodiments thereof, it will be understood by those skilled in the art that various changes in form and details may be made therein without departing from the scope of the invention encompassed by the appended claims.

Example 6

Push-Through Assay

A CPI3 peptide is a 5-histidine tagged version of the broad spectrum peptide CPI2 used for the detection of multiple pathogens. A cysteine group is was added on the N-terminal end to allow for labeling with dye:

(SEQ ID NO: 5)
CPI3[Ac]CGAMFLEAIPMSIPAAAAHHHHH-[OH]

The CPI3 peptide was labeled with tetramethylrhodamine iodoacetamide (TMRIA) dye (available from Molecular Probes. Eugene, Oreg.) on the cysteine group. The labeling reaction was performed in PBS pH 7.4 with an excess of TMRIA dye. The dye to peptide ratio was calculated to be about 1.0.

Approximately 1 mg of CPI3 labeled with TMRIA dye was bound to 1 ml nickel-nitrilotriacetic acid (Ni-NTA) agarose beads (obtained from Qiagen, Valencia, Calif.) through the 5-histidine tag on the peptide. Essentially all the CPI3 bound to the Ni-NTA beads, as evidenced by the loss of color from the solution.

A 50 µl bead volume of CPI3-TMRIA was placed in tubes and 200 µl of $1 \times 10^4$) or $1 \times 10^5$ cfu per mL *Enterococcus faecalis* was added and allowed to incubate for 5 minutes at room temperature. The bacterial proteases cleaved the CPI3 such that a dye-peptide fragment was released from the Ni-NTA beads. The beads were separated from solution through a short centrifugation with a microfuge.

Corresponding volumes and bacterial concentrations (e.g. 100 µl of $1 \times 10^5$ cfu/µl) to obtain $10^5, 10^6, 10^7$ cfu equivalents were removed from the tubes and placed in the tip of a 1 ml syringe. Phosphate buffered saline with no added bacteria was used as a control.

The syringe was then placed on top of a matching sized O-ring on a polyvinylidene fluoride (PVDF) membrane backed by filter paper and the plunger depressed to force the liquid through the membrane. Dye-peptide fragments were retained at the surface of the PVDF membrane and only un-dyed liquid passed through to the filter paper. After 5 minutes, the PVDF membrane exposed to the $10^7$ cfu/mL liquid exhibited the brightest color response, while the PVDF membrane exposed to the $10^6$ cfu/mL liquid exhibited less of a color response than the membrane exposed to the $10^7$ cfu/mL liquid. After 5 minutes, the PVDF membrane exposed to the $10^5$ cfu/mL liquid exhibited less of a color response than the membrane exposed to the $10^6$ cfu/mL liquid, while the membrane exposed to the 0 cfu/mL liquid exhibited no discernable color response.

Example 7

Stability of Detectably Labeled Substrates

Figure 11:
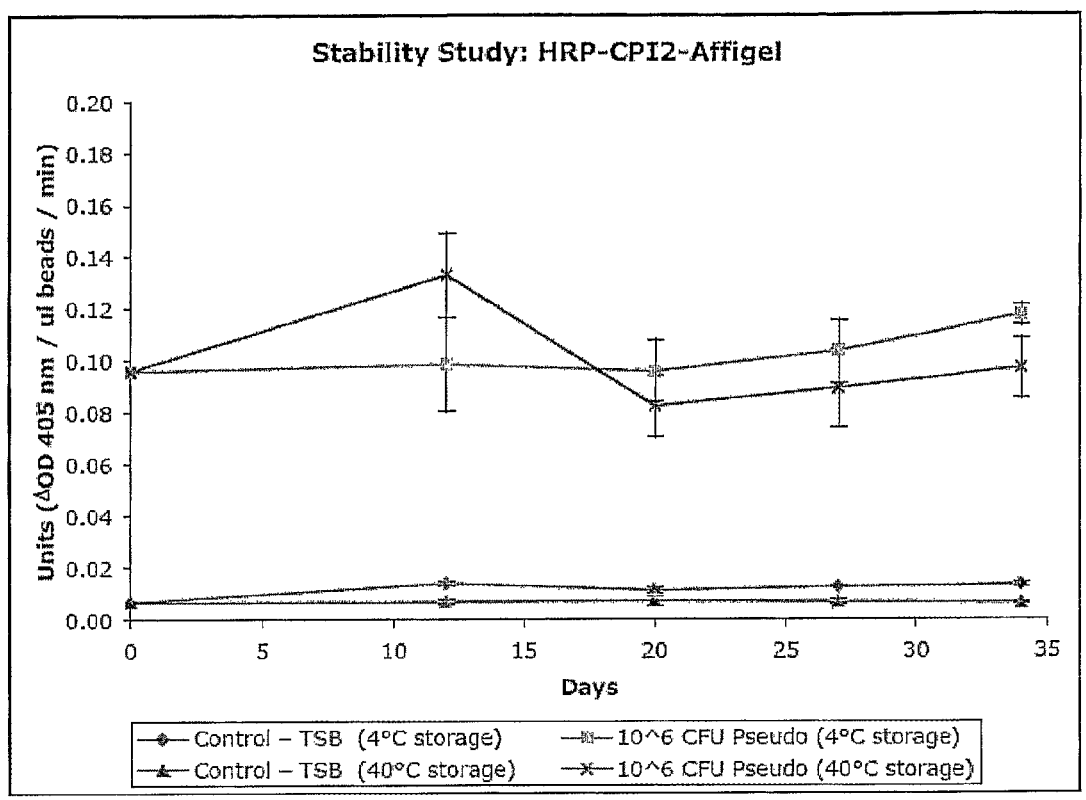
FIG. 11 illustrates a graph of fluorescent measured from various samples taken during a stability study.

To evaluate the long-term stability or viability of detectably labeled substrates, CPI2 substrates were detectably labeled with HRP and attached to AffiGel beads. The beads were aged at 40° C. for a total of 35 days. At various intervals along the 35-day ageing process, samples of the beads were taken and exposed to a solution containing $10^6$ CFU/ml of *P. aeruginosa* or a control buffer of PBS. The beads exposed to the bacterial gave a dark blue signal, while those exposed to the control did not. FIG. 11 illustrates a graph of the color measured of the various samples taken during the stability study. The data shows that the beads are very stable and do not have any problems with deterioration of the detectable signal over time, indicating that the beads are very durable.

Example 8

Inter-Strain Operability

Figure 12:
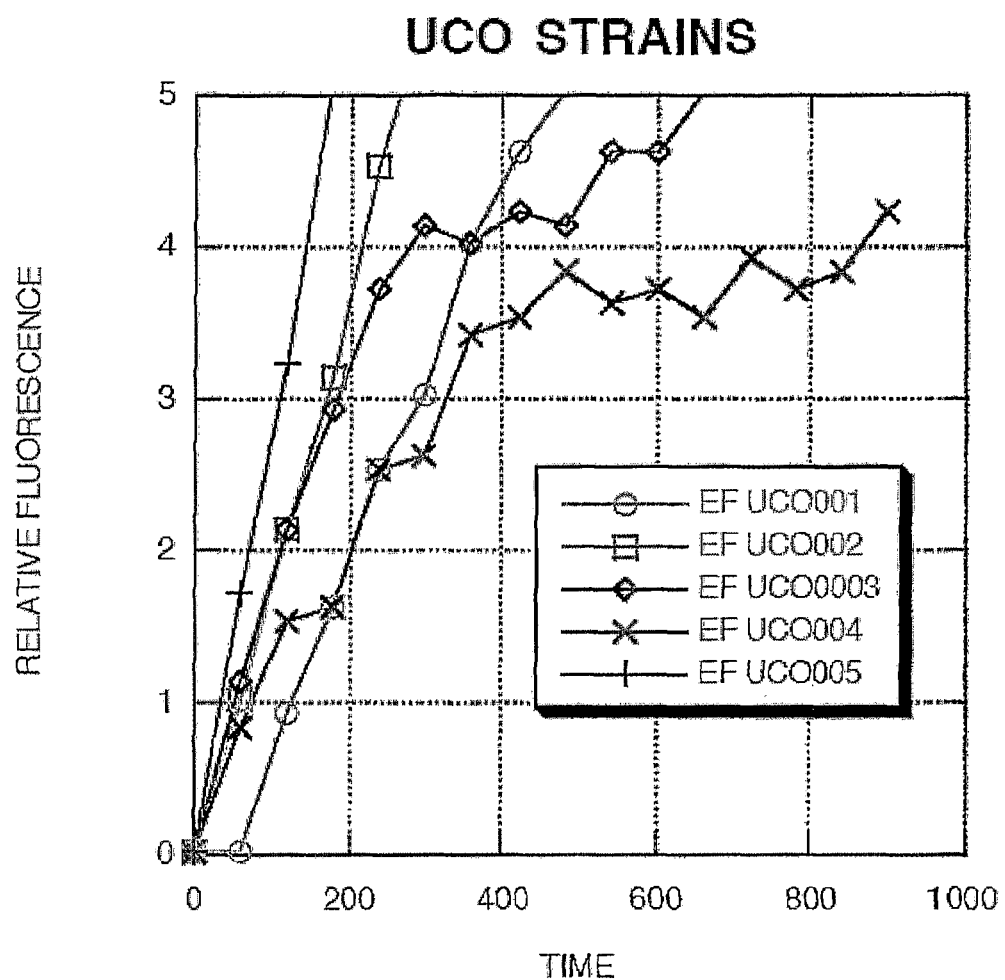
FIG. 12 illustrates a graph of relative fluorescence measured from a detectably labeled substrates after exposure to various strains of a wound pathogen.

A CIP2 fluorescent resonance energy transfer (FRET) peptide was exposed to five different clinical strains of *E. faecalis* (obtained from the University of Colorado). The peptide reacted strongly with all five strains. FIG. 12 illustrates a graph of the relative fluorescence measured after exposure to the various strains. The data indicates that the detectably labeled peptide will detect the presence of different strains of a wound pathogen.

Example 9

Reactivity of CPI2 Peptide Conjugated with HRP

The CPI2 peptide was conjugated with horse radish peroxidase (HRP), and then coupled to various beads (e.g., affigel and agarose beads) for liquid and solid phase assays. Some of the beads were exposed to a solution containing $10^6$ CFU/ml of *Pseudomonas aeruginosa*. A dark blue color formed in the presence of ABTS and hydrogen peroxide, indicating the presence of the bacteria. The detectable color signal worked in less than four minutes, suggesting that the detectably labeled beads could be used as a rapid broad spectrum point of care test useful for detecting harmful pathogens.

Example 10

Clinical Swab Sample Tests

The CPI2 peptide was conjugated with horse radish peroxidase (HRP), and then coupled to various beads (e.g., affigel and agarose beads) for liquid and solid phase assays. Swab samples that had been exposed to patient wounds were obtained from the University of Massachusetts Medical School. The swab samples were tested for the presence of bacteria with the following protocol:

1) The HRP-beads were diluted 1:10 with PBS to form a bead slurry. 10 microliters of the slurry was added to each well of a filter plate.

2) 10 microliters of each frozen wound sample were added to 80 microliters of PBS. The resulting solution was then added to a well in the filter plate.

3) The plate was incubated for four minutes, and then the filter was spun into another plate containing US Biological stable liquid substrate (1.46 mM ABTS and $H_2O_2$).

4) After one minute of development time, the microplate reader was read at 405 nm.

Samples that contained wound pathogens turned dark blue in the presence of ABTS and hydrogen peroxide.

We claim:

1. A method for detecting the presence or absence of a wound-specific bacterium, wherein the wound-specific bacterium is one or more of *Staphylococcus aureus, Streptococcus pyogenes, Pseudomonas aeruginosa, Enterococcus faecalis,* and *Serratia marcescens,* in a sample selected from a wound surface, a body fluid, or fluid from a wound, comprising:
    a) contacting the sample with a detectably labelled synthetic a1-proteinase inhibitor reactive site loop domain peptide substrate under conditions that result in cleavage of said substrate by an enzyme produced by the wound-specific bacterium; and
    b) detecting a cleavage or an absence of the cleavage of the substrate, the cleavage of the peptide substrate indicating the presence of the wound-specific bacterium in the sample and absence of cleavage of the substrate indicating absence of the wound-specific bacterium in the sample.

2. The method according to claim 1, wherein the enzyme is a protease.

3. The method according to claim 1, wherein the peptide substrate is labelled with a fluorescent probe and a quencher dye molecule.

4. The method according to claim 1, wherein the peptide substrate is labelled by a label selected from the group consisting of spin labels, antigen tags, epitope tags, haptens, enzyme labels, prosthetic groups, fluorescent materials, pH-sensitive materials, chemiluminescent materials, colorimetric components, bioluminescent materials, and radioactive materials.

5. The method according to claim 1, wherein the peptide substrate comprises at least one of the peptides selected from the group consisting of EAAGAMFLEAIPK (SEQ ID NO:1), EGAMFLEAIPMSIPK (SEQ ID NO:2), KGTEAAGAMFLEAIPMSIPPEVK (SEQ ID NO:3), GAMFLEAIPMSIPPE (SEQ ID NO:4), and CGAMFLEAIPMSIPAAAHHHHH (SEQ ID NO:5).

6. The method according to claim 1, wherein the peptide substrate is on a solid support.

7. The method according to claim 1, wherein the solid support is selected from the group consisting of a wound dressing, a container for holding body fluids, a disk, a scope, a filter, a lens, a foam, a cloth, a paper, a suture, a dipstick, a swab, a urine collection bag, a blood collection bag, a plasma collection bag, a test tube, a catheter, and a well of a microplate.

8. The method according to claim 1, wherein the solid support comprises a material required to be free of microbial contaminants.

9. The method according to claim 1, wherein the peptide substrate comprises at least two dissimilar colorimetric components and the peptide substrate is attached to a solid support, wherein modification of the peptide substrate comprises cleaving at least a portion of the peptide substrate that includes one of the colorimetric components, the cleaving resulting in a visible color change.

10. The method according to claim 1, wherein the colorimetric components are covalently attached to the peptide substrate.

11. A method for detecting the presence or absence of a wound-specific bacterium, wherein the wound-specific bacterium is one or more of *Staphylococcus aureus, Streptococcus pyogenes, Pseudomonas aeruginosa, Enterococcus faecalis*, and *Serratia marcescens*, in a sample selected from a wound surface, a body fluid, or fluid from a wound, comprising:
   a) contacting the sample with a detectably labelled synthetic α1-proteinase inhibitor reactive site loop domain peptide substrate set forth in SEQ ID NO:2 under conditions that result in cleavage of said peptide substrate by an enzyme produced by the wound-specific bacterium; and
   b) detecting a cleavage or an absence of the cleavage of the peptide substrate, the cleavage of the peptide substrate indicating the presence of the wound-specific bacterium in the sample and absence of cleavage of the peptide substrate indicating absence of the wound-specific bacterium in the sample.

12. The method according to claim 11, wherein the enzyme is a protease.

13. The method according to claim 11, wherein the peptide substrate is labelled with a fluorescent probe and a quencher dye molecule.

14. The method according to claim 11, wherein the peptide substrate is labelled by a label selected from the group consisting of spin labels, antigen tags, epitope tags, haptens, enzyme labels, prosthetic groups, fluorescent materials, pH-sensitive materials, chemiluminescent materials, colorimetric components, bioluminescent materials, and radioactive materials.

15. The method according to claim 11, wherein the colorimetric components are covalently attached to the peptide substrate.

* * * * *

SEQUENCE LISTING

```
<160> NUMBER OF SEQ ID NOS: 5

<210> SEQ ID NO 1
<211> LENGTH: 13
<212> TYPE: PRT
<213> ORGANISM: Artificial Sequence
<220> FEATURE:
<223> OTHER INFORMATION: Synthetic peptide sequence

<400> SEQUENCE: 1

Glu Ala Ala Gly Ala Met Phe Leu Glu Ala Ile Pro Lys
1               5                   10

<210> SEQ ID NO 2
<211> LENGTH: 15
<212> TYPE: PRT
<213> ORGANISM: Artificial Sequence
<220> FEATURE:
<223> OTHER INFORMATION: Synthetic peptide sequence

<400> SEQUENCE: 2

Glu Gly Ala Met Phe Leu Glu Ala Ile Pro Met Ser Ile Pro Lys
```

-continued

```
1               5               10              15
```

```
<210> SEQ ID NO 3
<211> LENGTH: 23
<212> TYPE: PRT
<213> ORGANISM: Homo sapiens

<400> SEQUENCE: 3

Lys Gly Thr Glu Ala Ala Gly Ala Met Phe Leu Glu Ala Ile Pro Met
1               5                   10                  15

Ser Ile Pro Pro Glu Val Lys
            20

<210> SEQ ID NO 4
<211> LENGTH: 15
<212> TYPE: PRT
<213> ORGANISM: Artificial Sequence
<220> FEATURE:
<223> OTHER INFORMATION: Synthetic peptide sequence

<400> SEQUENCE: 4

Gly Ala Met Phe Leu Glu Ala Ile Pro Met Ser Ile Pro Pro Glu
1               5                   10                  15

<210> SEQ ID NO 5
<211> LENGTH: 22
<212> TYPE: PRT
<213> ORGANISM: Artificial Sequence
<220> FEATURE:
<223> OTHER INFORMATION: Synthetic peptide sequence

<400> SEQUENCE: 5

Cys Gly Ala Met Phe Leu Glu Ala Ile Pro Met Ser Ile Pro Ala Ala
1               5                   10                  15

Ala His His His His His
            20
```